(12) United States Patent
van Dongen et al.

(10) Patent No.: US 11,442,060 B2
(45) Date of Patent: Sep. 13, 2022

(54) METHODS AND MEANS FOR MONITORING DISRUPTION OF TISSUE HOMEOSTASIS IN THE TOTAL BODY

(71) Applicants: Erasmus University Medical Center Rotterdam, Rotterdam (NL); Universidad De Salamanca, Salamanca (ES)

(72) Inventors: Jacobus Johannes Maria van Dongen, Vorden (NL); Jose Alberto Orfao de Matos Correia e Vale, Salamanca (ES)

(73) Assignees: Erasmus University Medical Center Rotterdam, Rotterdam (NL); Universidad De Salamanca, Salamanca (ES)

( * ) Notice: Subject to any disclaimer, the term of this patent is extended or adjusted under 35 U.S.C. 154(b) by 0 days.

(21) Appl. No.: 16/742,583

(22) Filed: Jan. 14, 2020

(65) Prior Publication Data
US 2020/0191777 A1    Jun. 18, 2020

Related U.S. Application Data

(62) Division of application No. 14/002,879, filed as application No. PCT/NL2012/050132 on Mar. 5, 2012, now abandoned.

(30) Foreign Application Priority Data

Mar. 4, 2011   (EP) .................................... 11157001

(51) Int. Cl.
*G01N 33/50* (2006.01)
*G01N 33/569* (2006.01)

(52) U.S. Cl.
CPC ..... *G01N 33/5094* (2013.01); *G01N 33/5091* (2013.01); *G01N 33/56972* (2013.01); *G01N 2800/52* (2013.01)

(58) Field of Classification Search
CPC ........... G01N 2800/52; G01N 33/5091; G01N 33/5094; G01N 33/56972
See application file for complete search history.

(56) References Cited

U.S. PATENT DOCUMENTS

| 4,208,479 A | 6/1980 | Zuk et al. |
| 2007/0243599 A1 | 10/2007 | Popma |
| 2011/0195437 A1* | 8/2011 | Brozek .............. G01N 33/5055 435/7.92 |

FOREIGN PATENT DOCUMENTS

| EP | 2259065 A1 | 8/2010 |
| WO | WO 2010/015633 * | 2/2010 |
| WO | 2010140885 A1 | 12/2010 |

OTHER PUBLICATIONS

Memorandum "Clarification of Written Description Guidance For Claims Drawn to Antibodies and Status of 2008 Training Materials," dated Feb. 22, 2018.*
Edwards et al., "The remarkable flexibility of the human antibody repertoire; isolation of over one thousand different antibodies to a single protein, BlyS," J. Mol. Biol., 2003, vol. 334, pp. 103-118.*
Van den Bossche et al., "Monocytes carrying GFAP detect glioma, brain metastasis and ischaemic stroke, and predict glioblastoma survival," Brain Comm., 2021, vol. 3, issue 1, pp. 1-12.*
Herwig et al., "Detecting prostate cancer by intracellular macrophage prostate-specific antigen (PSA): a more specific and sensitive marker than conventional serum total PSA", Eur. J. Clin. Invest., 2008, vol. 38, No. 6, pp. 430-437.*
Jung, C. S., et al., "Serum GFAP is a Diagnostic Marker for Glioblastoma Multiforme," Brain 130, No. 12 (2007): 3336-3341.
Autissier, Patrick, et al., "Evaluation of a 12-Color Flow Cytometry Panel to Study Lymphocyte, Monocyte, and Dendritic Cell Subsets in Humans," Cytometry Part A: The Journal of the International Society for Advancement of Cytometry 77, No. 5 (2010): 410-419.
Clark, Georgina J., et al., "Monocytes Immunoselected Via the Novel Monocyte Specific Molecule, CD300e, Differentiate into Active Migratory Dendritic Cells," Journal of Immunotherapy 30, No. 3 (2007): 303-311.
Van De Loosdrecht, et al., "Standardization of Flow Cytometry in Myelodysplastic Syndromes: Report from the First European LeukemiaNet Working Conference on Flow Cytometry in Myelodysplastic Syndromes," Haematologica 94, No. 8 (2009): 1124-1134.
Brckalo, Tamara, et al., "Functional Analysis of the CD300e Receptor in Human Monocytes and Myeloid Dendritic Cells," European Journal of Immunology 40, No. 3 (2010): 722-732.
Japink, D., et al., "T1118 CEA in Activated Macrophages: A New Prognostic or Diagnostic Factor for Early Detection of Local Recurrence of Colorectal Neoplasms?" Gastroenterology 134, No. 4 (2008): p. 487, XP123434076.
Herwig, R., et al., "Differentiation Enhancement of Circulating Immune Cells Containing Intracellular PSA: A New Method for Discrimination Between Benign and Malignant Prostatic Disease," European Urology Supplements 5, No. 2 (2006): 275, XP005522982.
Herwig, Ralf, et al., "Immunological Reaction in Different Stages of Prostate Cancer Under Various Therapies Measured by IMPSA and Serum Total PSA," The Journal of Urology 4, No. 181 (2009): p. 653.
Aguilar, Helena, et al., "Molecular Characterization of a Novel Immune Receptor Restricted to the Monocytic Lineage," The Journal of Immunology 173, No. 11 (2004): 6703-6711.
Clark, Georgina, et al., "Eighth Leucocyte Differentiation Antigen Workshop DC Section Summary," Cellular Immunology 236, No. 1-2 (2005): 21-28.

\* cited by examiner

*Primary Examiner* — Galina M. Yakovleva
(74) *Attorney, Agent, or Firm* — Hoffmann & Baron, LLP

(57) ABSTRACT

The invention relates to the field of medical diagnostics. Provided are methods and kits for determining the health status of a subject, for early detection of tissue damage, for early diagnosis and monitoring of a disease, and/or for evaluation of treatment effectiveness in a subject using circulating tissue macrophages (CTM) as a mirror of disrupted tissue homeostasis and disease.

8 Claims, 9 Drawing Sheets

Figure 1:
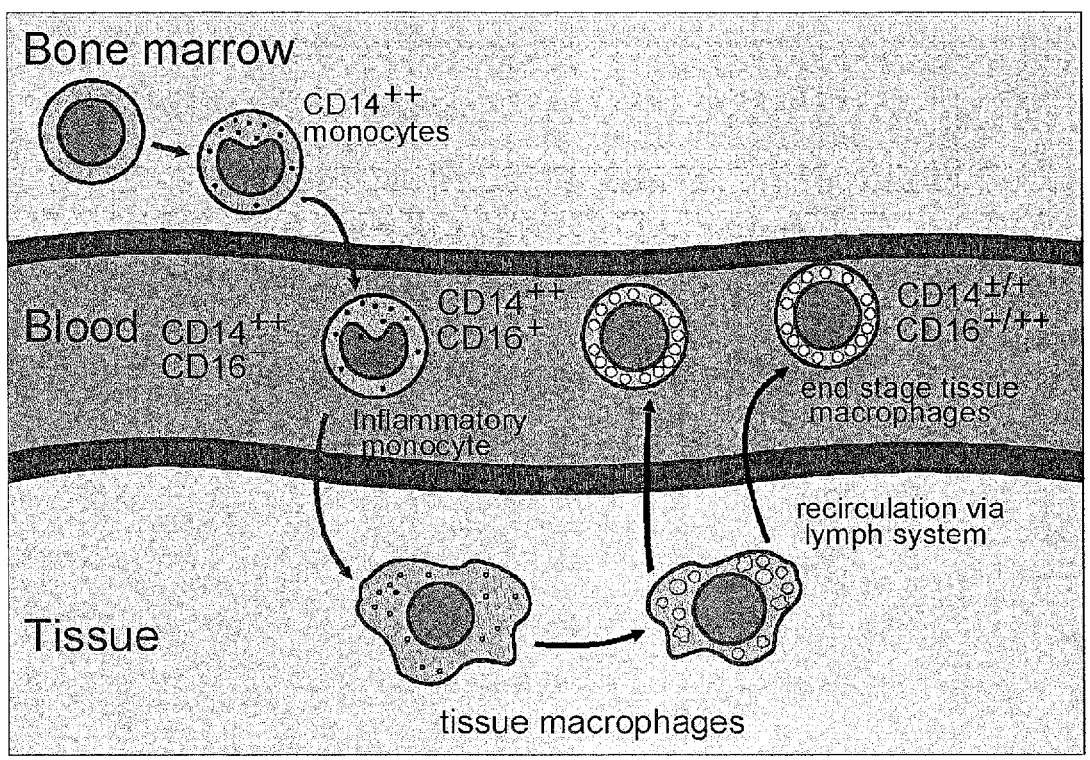

METHODS AND MEANS FOR MONITORING DISRUPTION OF TISSUE HOMEOSTASIS IN THE TOTAL BODY

This application is a divisional of, and Applicants claim priority from, U.S. Ser. No. 14/002,879 filed Oct. 3, 2013, which is the U.S. National Phase of, and Applicants claim priority from, International Application No. PCT/NL2012/050132 filed Mar. 5, 2012, which claims priority from European Application No. EP 11157001.6, each of which are incorporated herein by reference.

BACKGROUND OF THE INVENTION

The invention relates to the field of medical diagnostics. It provides new tools including diagnostic kits and methods for total body scan aiming at inter alia evaluation of physiological processes, lifestyle-related and, environmental exposures, early diagnosis and monitoring of diseases, and their treatment.

Full-body scan is a scan of the subject's entire body to support the diagnosis and treatment of healthy conditions and illnesses. It may also be known as a full-body CT scan if computed tomography (CAT) technology is used, though there are many types of medical imaging technology which can perform full-body scans. A full-body scan can theoretically catch deadly diseases (e.g. cancer) in early stages, which can save lives. However, in practice, the benefits of currently known total body scans may not outweigh the risks and costs. Thus, controversy arises from the use of full-body scans in the screening of patients who have not been diagnosed with a disease, or who do not have symptoms suggestive of a disease. As with any test that screens for disease, the risks of full-body CT scans need to be weighed against the benefit of identifying a treatable disease at an early stage. Compared to most other diagnostic X-ray procedures, CT scans result in relatively high radiation exposure, which may be associated with a very small yet significant increase in the possibility of developing cancer later in a person's life. Importantly, current imaging techniques require expensive equipment with which only one subject can be analysed at a time. In contrast, blood testing can be performed in parallel for many individuals and instrumentation required is widely available in many diagnostic laboratories. In addition, for blood testing the patient does not need to travel to the screening center, but local collection and subsequent transportation of a blood sample is sufficient.

DESCRIPTION OF THE INVENTION

The present inventors recognized the need for alternative means and methods to scan a subject's entire body wherein the risk is greatly outweighed by the benefit of identifying a treatable disease at an early stage. They developed a conceptually novel system for total body scan aimed at evaluation of physiological processes, screening of health status in general, and early diagnosis and monitoring of diseases and their management (e.g. treatment). It involves a Flow Cytometric Body Scan (FlowBoScan) or Tissue Macrophage Scan (TiMaScan) using tissue macrophages in blood as a mirror of disrupted tissue homeostasis and disease. The novel tool does not involve any body exposure to harmful radiation. In contrast, the TiMaScan can be performed on readily accessible body samples, such as peripheral blood.

All tissue compartments in human and animal bodies are maintained by a delicate homeostatic balance of cell proliferation and cell death, mainly programmed cell death by apoptosis (type I) and autophagy (type II). Dependent on the type of tissue, the homeostasis activities are higher or lower. For example, epithelial cells in the gut, hematopoietic cells in the bone marrow, and skin epithelium have a high turnover, whereas this turnover is lower in other tissues such as the nervous system, liver, kidney, and muscles. Nevertheless in all tissues the cellular homeostasis is being maintained, whether this is at a high or a lower level of homeostasis. On top of the basic level of homeostasis, activation, regeneration, and senescence processes influence the homeostasis of proliferation and cell death leading to expansion or involution. For example, activation by frequent usage will increase the basic homeostasis level to a higher homeostasis level, such as increase in muscle volume and composition via specific physical training in sports and involution of such muscles when training is discontinued. Also wear and tear of the skin by hard labor or chemical exposures will thicken the skin of palms and soles, which callus will disappear when the wear and tear is abolished.

Specific conditions can change or even disrupt the level of cellular homeostasis, such as:
- tissue damage (trauma or surgical intervention) and subsequent repair;
- functional stress of organ systems, such as alcohol abuse and liver dysfunction or marathon and triathlon participation and muscle exhaustion;
- (premature) age-related involution (senescence);
- suppression and subsequent regeneration, e.g. by drugs such as corticosteroids;
- inflammation and subsequent repair by regeneration and/or fibrosis, e.g. in autoimmune diseases;
- infectious diseases with a persisting smoldering and insidious character, such as tuberculosis, Lyme's disease, Q fever, etc;
- dysregulation of proliferation, followed by hyperplasia and potentially also followed by dysplasia and malignant transformation.

Despite high levels of homeostatic proliferation and apoptosis, dead cells or dying cells are rarely observed in tissue sections. Apparently, the dead cells and apoptotic cells are removed fast and efficiently by the tissue macrophages. It is fair to assume that each individual tissue macrophage serves a particular (limited) area in the involved tissues and can remove the apoptotic cells and other tissue damage efficiently. Since each tissue macrophage most likely handles a limited number of apoptotic cells (e.g. 20 to 40 cells, dependent on the size and type of cells), the volume/size of the surveillance area is dependent on the type of tissue and the homeostatic activity level of the involved tissue. The higher the homeostasis level or the higher the repair or proliferation level, the more tissue macrophages are needed, to keep the involved tissue debris-free and to avoid structural tissue alterations with functional impairment of the tissue. Consequently the number of tissue macrophages per tissue volume can vary dependent on the type of tissue, the activity of the tissue, the occurrence of inflammation or repair after damage, etc. As soon as the tissue macrophages have fulfilled their local task in their space of action, these end-stage macrophages leave their site of action and migrate via the lymph vessels to the blood stream, to be removed from the body, probably in the spleen.

The monocytic differentiation pathway in bone marrow continuously produces the CD14high/CD16-classical monocytes ("tissue-influx" monocytes), which become available in blood and can be recruited as inflammatory monocytes into affected tissues, where they mature into a heterogeneous (het) population of CD14high/CD16+ and CD14high/

CD16high tissue macrophages (FIG. 1). As soon as these cells have completed their surveillance and phagocytosis tasks, they become end-stage macrophages and migrate via the lymph vessel system as CD14het/CD16het CTMs to the blood stream ("tissue-efflux" monocytes/macrophages), where they are fragile cells and have a short life-span (FIG. 1).

Figure 2:
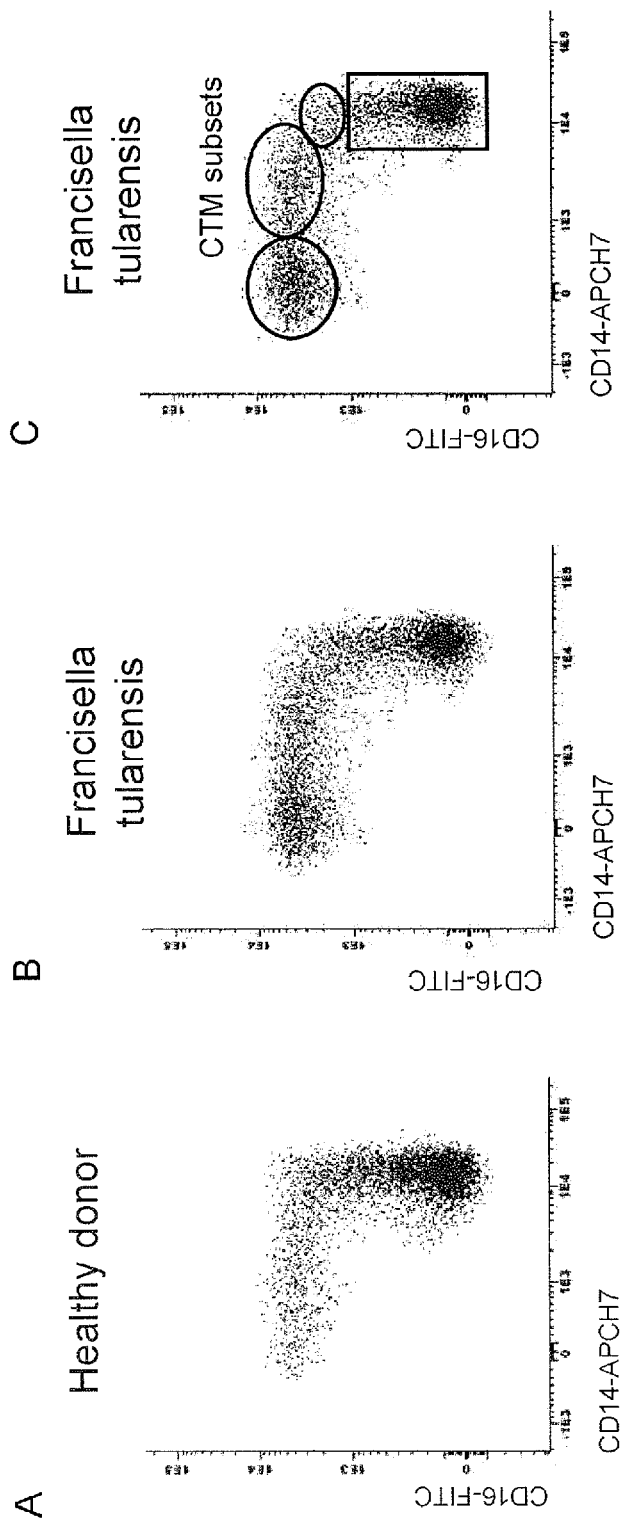

At least in part, the CTMs are detectable in peripheral blood. In normal blood, a small population of CTM is detectable, having a heterogeneous CD14 and CD16 expression. These CTMs are increased during ageing and in specific clinical conditions, e.g. after stem cell transplantation (SCT) and in case of inflammation, sepsis, cancer and excessive exercise (FIG. 2).

The presumed migration and recirculation process is supported by the finding that the relative frequencies of the classical monocytes and CTMs differ per site: low frequencies of the heterogeneous CD14+/CD16+ and CD14dim/CD16high CTMs in bone marrow and blood, but higher frequencies in lymph fluid (Table 1) (Orfao et al., unpublished results).

TABLE 1

Relative frequencies of classical monocytes and CTMs*

| | CD14high/CD16−<br>classical monocytes | CD14+/CD16+ and<br>CD14dim/CD16high CTMs |
|---|---|---|
| Bone marrow | ~95% | ~5% |
| Cord blood | 90-95% | 5-10% |
| Adult blood | 80-90% | 10-20% |
| Lymph | 5-35% | 65-95% |

*Orfao et al., unpublished results

It is fair to assume that both in healthy persons and in disease conditions the set of protein fragments and peptides in the phagosomes of each tissue macrophage consists of tissue-specific peptides, since the surveillance area of the tissue macrophages is most likely limited to one tissue type, probably even to a small tissue area within the involved tissue. Consequently, the total population of CTMs in blood at a given moment reflects the homeostatic level of all tissues in the total body. Based on the set of phagosomal peptides, each individual CTM should be assignable to its tissue of origin. The relative composition of the circulating tissue-specific macrophages (CTSM) is likely to be stable in relative and absolute numbers in blood as well as in their contents of different tissue-derived protein fragments and peptides, albeit that age-related, sex-related, metabolic-related and activity-related differences will occur, because such differences influence cellular homeostasis. Importantly, homeostatic changes (such as tissue damage) at any site in the body will lead to a change in relative and absolute numbers and in the relative composition of the intracellular levels of protein-fragments and peptides in the population of circulating tissue macrophages. Such changes may involve one or more distinct subsets of CTM and CTSM and they may include absence of a normally expressed epitope, aberrant expression of a normally absent epitope or altered levels of expression of a normally expressed epitope.

In the present invention we developed a system, using a unique combination of cell surface markers, for detection and identification of circulating tissue macrophages (CTMs) and their subsets in blood which is focused on the recognition of epitopes on products derived from intracellular processing and degradation (e.g. by one or more proteases) of proteins (e.g. peptides) that have been captured locally at the tissue, by single CTMs. The specific power of the novel system concerns the possibility to screen the whole CTM compartment in a blood sample for the origin of the individual CTM subsets and to define these subsets based on combinations of multiple tissue-specific protein fragments or peptides; in addition, further subsetting of these circulating tissue-specific macrophages (CTSM) may be based on the expression of other peptides such as those derived from aberrantly expressed proteins such as oncoproteins. In this way, the total CTM compartment reflects (mirrors) the ongoing processes in the various tissues of the total body, whether homeostatic or disturbed. These CTM subset measurements allow for the monitoring of health status and screening for specific diseases, including the tissue localization of these diseases. As soon as the diagnosis has been made, the monitoring of the relevant CTM subset can be used for follow-up of the individual status over time, e.g. to assess the disappearance or stability of a disease and/or to evaluate treatment effectiveness.

Hence, in one embodiment the invention provides a method for determining the health status of a subject, for early detection of tissue damage, for early diagnosis and monitoring of a disease, and/or for evaluation of treatment effectiveness in a subject using circulating tissue macrophages (CTM) as a mirror of disrupted tissue homeostasis and disease, the method comprising the steps of:

a) Providing a biological test sample from the subject, preferably a human subject, which contains circulating tissue macrophages (CTM);

b) staining of said CTM with a panel of differentially-labeled distinct antibodies against a set of backbone markers, aimed at the identification and enumeration of at least one, preferably at least two, CTM subset(s), wherein the backbone markers are CD14, CD16, and IREM2 (CD300e) and preferably also HLADR and/or CD45;

c) fixation, permeabilization and staining of the CTM using one or more detecting antibodies directed against one or more epitopes on at least one protease-induced protein fragment derived from intracellular degradation of a non-CTM protein by individual CTM in their tissues of origin, thereby identifying at least one subset of circulating tissue-specific macrophages (CTSM);

d) multiparameter flow-cytometric analysis of said stained CTM and CTSM to determine the amount of signals of each distinct labeled antibody associated with individual cells;

e) determining the relative and absolute number of individual cells within the CTM subset and specific subset(s) of CTSM that express each of the measured intracellular epitopes;

f) calculating (i) the relative and absolute number of cells within the CTM subset and specific subset(s) of CTSM which each originate from different normal and altered tissues as defined by a set of individual protease-induced protein fragments evaluated, and ii) the amount of antibody-related signal associated to every individual intracellular peptide evaluated to obtain a test CTSM staining profile, and;

g) comparing the test CTSM staining profile with a normal CTSM staining profile for each tissue evaluated, wherein an aberrant test staining profile is indicative of tissue damage, an altered tissue homeostasis, the presence of a disease, and/or treatment effectiveness versus resistance.

IREM2 stands for "immune receptor expressed by myeloid cells 2". In the nomenclature of CD antigens this protein has been given the designation CD300E or CD300e. The protein is known also as CD300LE [CD300 molecule-like family member LE]. IREM2 expression appears to be restricted to monocytes, macrophages and dendritic cells and is down regulated upon differentiation.

HLADR is a MHC class II cell surface receptor encoded by the human leukocyte antigen complex on chromosome 6 region 6p21.31. HLADR is a αß heterodimer, cell surface receptor, each subunit contains 2 extracellular domains, a membrane spanning domain and a cytoplasmic tail. Both α and ß chains are anchored in the membrane. The complex of HLADR and its ligand, a peptide of 9 amino acids in length or longer, constitutes a ligand for the T-cell receptor (TCR).

As used herein, the abbreviation "CTM" stands for circulating tissue macrophages. "CTM subsets" refers to various subsets of CTM, including CD14high/CD16+, CD14high/CD16high, CD14+/CD16high, CD14low/CD16high, CD14−/CD16high, CD14−/CD16low CTMs, CD11c+/CD16+, CD11c+/CD16high, CD11c+/CD16low CTMs, CD33high/CD16+, CD33high/CD16high, CD33+/CD16high, CD33+/CD16low CTMs, CD300e+/CD16+, CD300e+/CD16high, CD300e+/CD16low CTMs, CD16+, CD16high, CD16low CTMs, CD14high/CD16+/CD300e+/HLADR+, CD14high/CD16high/CD300e+/HLADR+, CD14+/CD16high/CD300e+/HLADR+, CD14−/CD16high/CD300e+/HLADR+, and CD14−/CD16low/CD300e+/HLADR+ CTM's.

"CTSM" refers to circulating tissue-specific macrophages, for which the tissue-specificity is defined by intracellular staining of protease-digested fragments (peptides) from tissue-specific proteins. "Protease-induced protein fragments" are fragments or peptides derived from non-CTM proteins that have been ingested, processed and digested by the proteases in the phagosomes of macrophages. The expression "Backbone markers" refers to a recurrent set of markers for identification and enumeration of the CTM compartment and the CTM subsets; on top of these markers, additional membrane markers and intracellular stainings can be used for identification of CTM subsets, particularly the tissue-specific macrophages, the so-called CTSM subsets.

Figure 3:
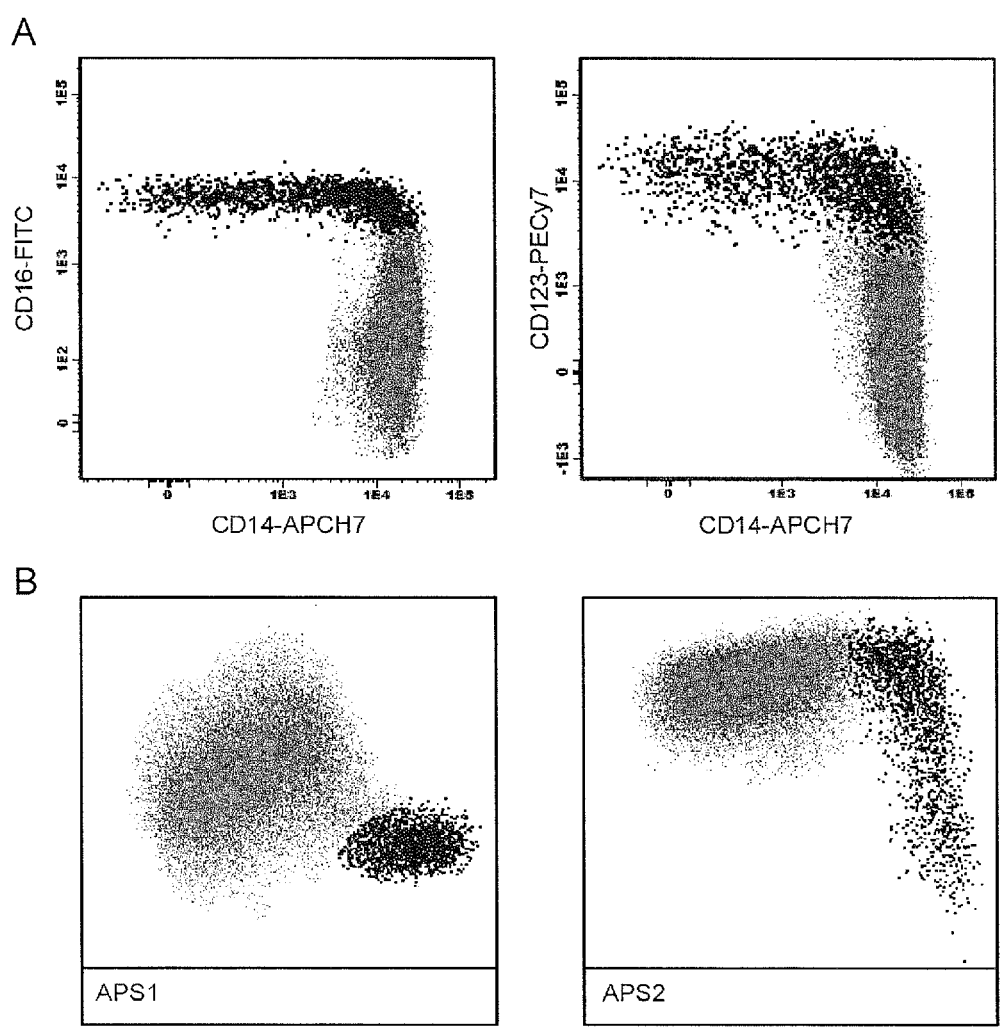

According to the invention, the set of backbone markers comprises at least antibodies directed at markers CD14, CD16 and CD300e, preferably supplemented with HLADR and/or CD45. In one embodiment, the combination of CD14, CD16 and CD300e is used. In another embodiment, the combination of CD14, CD16, CD300e and HLADR is used. Preferably, it furthermore comprises antibodies directed at one or more of the CD11c, CD33, CD35, CD36, CD45 and CD64 markers. CD45, CD36 and/or CD64 antibodies are particularly preferred. Very useful antibody panels comprise or consist of antibodies against CD14, CD16, CD300e and CD64; CD14, CD16, HLADR and CD64; CD14, CD16, CD300e, HLADR and CD64; CD14, CD16, CD300e, HLADR and CD45; CD14, CD16, CD300e, HLADR, CD64 and CD36. In one aspect, staining of the CTMs is performed with a panel of differentially-labeled distinct antibodies against the markers CD14, CD16, CD11c, CD33, CD36, CD45, CD64, CD123, CD86, CD300e, and HLA-DR. In a specific aspect, staining of the CTMs is performed with a panel of differentially-labeled distinct antibodies against the markers CD14, CD16, CD300e, HLADR, CD45, CD64 and CD36 This allows precise gating of all monocytes and all CTMs, accurate discrimination between monocytes and CTMs, and subsetting of CTMs (FIG. 3).

The analysis of macrophages for ingested proteins of non-macrophage origin has been described in the art. However, the advantage of flow cytometric subsetting of a macrophage target population based on the positive selection of cells expressing at least three specific surface markers (CD14, CD16, CD300e plus HLA-DR and/or CD45) according to the present invention has never been described or suggested.

Japink et al. (Gastroenterology, Elsevier, Vol. 134, no. 4, (2008 Apr. 1), page A-487) discloses the determination of intracellular carcinoemyonic antigen (CEA) in CD14+/CD16+cells from blood samples by flow cytometry for early detection or recurrence of colorectal neoplasms.

Herwig et al. (European Urology Suppl., Vol. 5, No. 2, (2006 Apr. 1), page 275, XP005522982; and J. of Urology, Vol. 181, No. 4 (2009 Apr. 1), pg. 653, XP025979386) discloses multicolor flow cytometric analysis CD14+/CD16+ peripheral blood mononuclear cells for intracellular PSA in the diagnosis of prostate cancer.

WO2010/015633 describes a method for characterizing molecular markers that are intracellularly absorbed from tissues by blood macrophages that are recirculated from the tissue into the circulatory system. To that end, a CD14/CD16-positive target population is defined, optionally in combination with the negative selection of CD56, CD57 and/or CD161 expressing cells.

WO2009/1000953 relates to the analysis of activated macrophages (CD14/CD16) for intracellular fragments of A beta fragments. A beta fragments are detected by MALDI-TOF-MS following cell lysis to generate of a pooled cell lysate and immunoprecipitation. A combination of antibodies against CD45, CD14, CD16 and CD19 is used to identify activated macrophages and the B-cell population.

Almeida et al. (Clin. Immunol. Vol. 100, No. 3, pp. 325-338, 2001) performed a comparative analysis of the morphological, cytochemical, immunophenotypical, and functional characteristics of normal human peripheral blood lineage(−)/CD16(+)/HLA-DR(+)/CD14(low) cells, CD14(+) monocytes, and CD16(−) dendritic cells. Disclosed is the cell sorting of mononuclear cells using a combination of antibodies against CD14, CD16 and HLADR, plus other lineage specific markers (e.g. CD3 for exclusion of T-lymphocytes, CD19 to exclude B-cells and CD56 to exclude NK-cells). The sorted cells are subsequently analysed by morphological and cytochemical examination of monocyte-specific characteristics. Nothing is mentioned or suggested about intracellular staining for processed, tissue-specific proteins.

Figure 4:
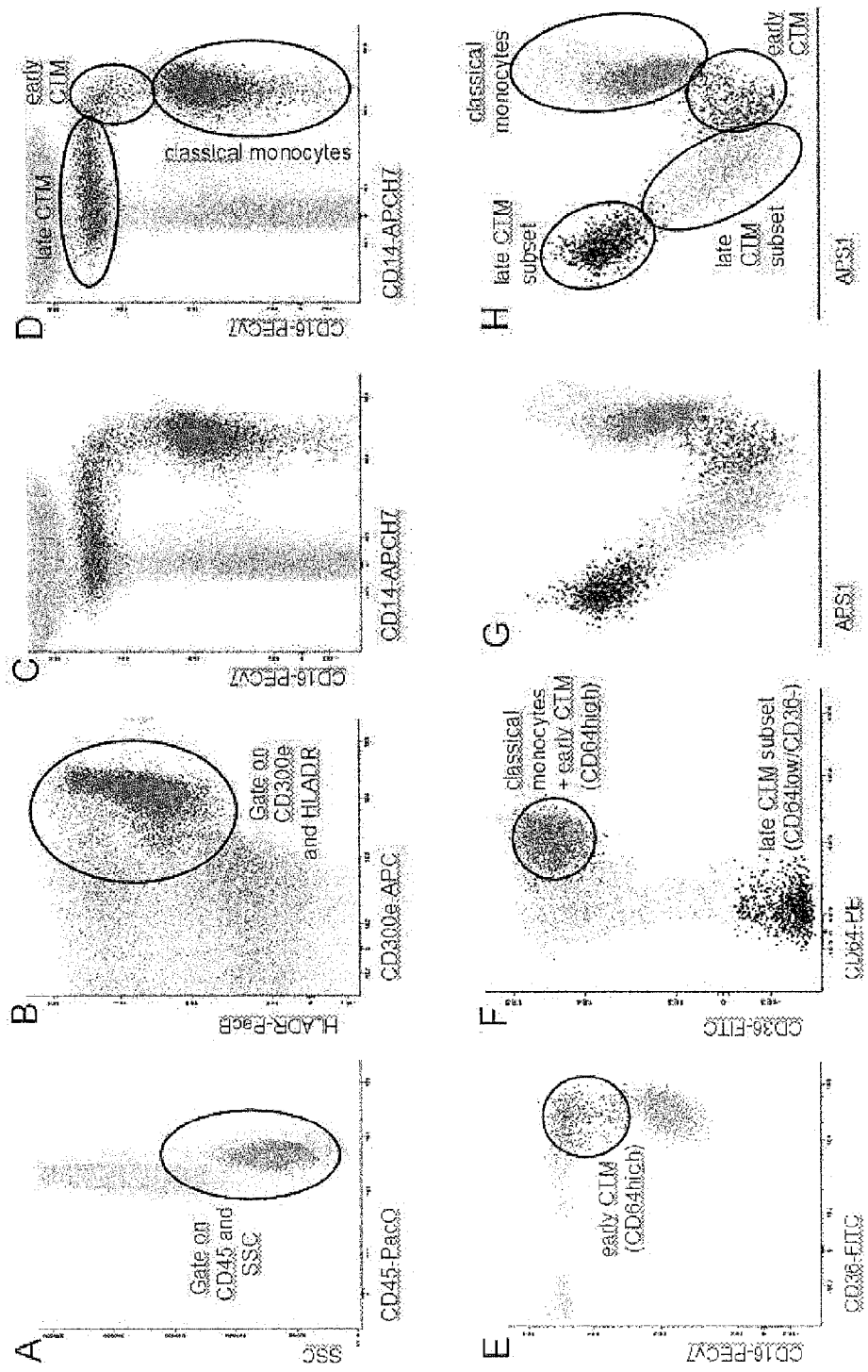

The multicolor flow cytometric method provided herein preferably comprises specific gating strategies based on the cell surface expression of CD14, CD16 and CD300e (IREM2), preferably CD14, CD16, CD300e (IREM2) and HLADR, in combination with side scatter (SSC) analysis (FIG. 4). The gating strategies for the monocyte-macrophage cell populations are composed of an inclusion step and a subset identification step. The inclusion step aims at inclusion of both the "classical monocytes" ("tissue-influx" monocytes) plus tissue macrophages ("tissue-efflux" monocytes/macrophages=circulating tissue macrophages; CTM). The subsequent steps should discriminate the classical monocytes from CTMs and should particularly identify subsets within the CTM population. Hence, in one embodiment of the invention the gating strategy comprises (i) an inclusion gating strategy to include both classical monocytes and CTMs, followed by (ii) a subset identification gating strategy to discriminate classical monocytes from CTMs and to identify one or more subsets within the CTM population.

Various gating strategies can be envisaged. The most simple strategy for detection of all classical monocytes and the vast majority of CTM's and some CTM subsetting comprises staining with at least CD14, CD16 and CD300e. All classical monocytes and most (not all) CTMs are detected by gating on a combination of side scatter (SSC) plus CD300e (IREM2)+cells (select cells with low to intermediate SSC that express CD300e). A more accurate strategy for detection of all classical monocytes and the virtually all CTM's and some CTM subsetting comprises staining with at least CD14, CD16, CD300e and HLADR. All classical monocytes plus virtually all CTMs are detected by gating on a combination of side scatter (SSC) plus CD300e and HLADR (i.e. select cells with low to intermediate SSC that simultaneously co-express CD300e and HLADR). A highly accurate strategy for detection of all classical monocytes and all CTM's and some CTM subsetting comprises staining with at least CD14, CD16, CD45, CD300e and HLADR. All influx and all efflux monocytes/macrophages can be detected by gating on a combination of side scatter (SSC) plus CD45, CD300e and HLADR positive cells. More specifically, cells with CD45 and low to intermediate SSC are selected that simultaneously co-express CD300e and HLADR (FIGS. 4A and B). Accordingly, the inclusion step may comprise either one of the following:

(i) staining with at least CD14, CD16 and CD300e and gating on a combination of SSC plus CD300e+ cells to select cells with low to intermediate SSC that express CD300e;

(ii) staining with at least CD14, CD16, CD300e and HLADR and gating on a combination of side scatter (SSC) plus CD300e and HLADR+ cells to select cells with low to intermediate SSC that simultaneously co-express CD300e and HLADR; or (iii) staining with at least CD14, CD16, CD45, CD300e and HLADR and gating on a combination of SSC plus CD45, CD300e and HLADR positive cells, preferably gating on cells with CD45 and low to intermediate SSC that simultaneously co-express CD300e and HLADR (FIG. 4A to D).

The invention also provides several gating strategies for CTM subset identification. In one embodiment, the strategy allows the identification of classical monocytes (CD14+/CD16−) and some CTM subsets. The CTM subsets are defined within one of the above inclusion gates, preferably using at least SSC, CD300e and HLADR, based on the additional usage of at least CD14 and CD16. Accordingly, in one embodiment the gating strategy comprises the identification of classical (CD14+/CD16−) monocytes and two main CTM subsets identified as CD14high/CD16low to CD14high/CD16high, and CD14low/CD16high to CD14−/CD16high and CD14−/CD16low (FIG. 4D).

In another embodiment, the subset gating strategy consists of three steps, which allow a more accurate detection of classical monocytes and several CTM subsets within one of the above inclusion gates (preferably using at least SSC, CD300e and HLADR), based on the additional usage of at least CD14, CD16 and CD64.

In the first step, the classical monocytes and the more mature CTM stages are being identified via gating on CD64low (late stage CTM) versus CD64high (classical monocytes plus early stage CTM). The second step aims at the discrimination between monocytes and CTM via selection for all other early CTM cells (vs. classical monocytes) as those events carrying a CD16+/CD14+ phenotype. Consequently the selected cells, defined as CD64low and as CD16+/CD64high would constitute the whole CTM compartment, while all other gated cells selected in the general gating step would correspond to classical monocytes. In the third step, based on the expression levels of CD64, CD14 and CD16 among the selected CTM may be further subdivided into distinct functional or maturation-associated compartments: from CD64high/CD14high/CD16low to CD64high/CD14high/CD16high, CD64high/CD14low/CD16high, CD64low/CD14−/CD16high and CD64low/CD14−/CD16low. Accordingly, in one aspect the subset identification step comprises:

gating on CD64low representing late stage CTM versus CD64high representing classical monocytes plus early stage CTM, followed by discriminating between monocytes and CTM via selection for all other early CTM cells (vs. classical monocytes) as those events carrying a CD16+/CD14+ phenotype and defining whole CTM compartment as CD64low and as CD16+/CD64high, followed by further subdividing the selected CTM based on the expression levels of CD64, CD14 and CD16 into distinct functional or maturation-associated compartments, preferably wherein the distinct compartments are CD64high/CD14high/CD16low to CD64high/CD14high/CD16high, CD64high/CD14low/CD16high, CD64low/CD14−/CD16high and CD64low/CD14−/CD16low.

In still a further embodiment, the invention provides a strategy that allows for the extra subsetting of the CTM population, which might be valuable in case of specific samples (e.g. childhood peripheral blood or adult bone marrow) containing precursors of classical monocytes. Usage of CD36 in combination with CD64 contributes to better identify all maturation stages of both the classical monocytes and CTM in the third step of the preceding strategy with the following subpopulations (FIG. 4E to H):

Classical monocytes: CD64high/CD36lo (precursors of classical monocytes) to CD64high/CD36high cells (real mature monocytes);

CTM subsets: from CD64high/CD36high/CD14high/CD16low to CD64highCD36high/CD14high/CD16high, CD64high/CD36highCD14low/CD16high and CD64low/CD36high/CD14−/CD16high to CD64low/CD14−/CD16low/CD36− to low cells.

Figure 5:
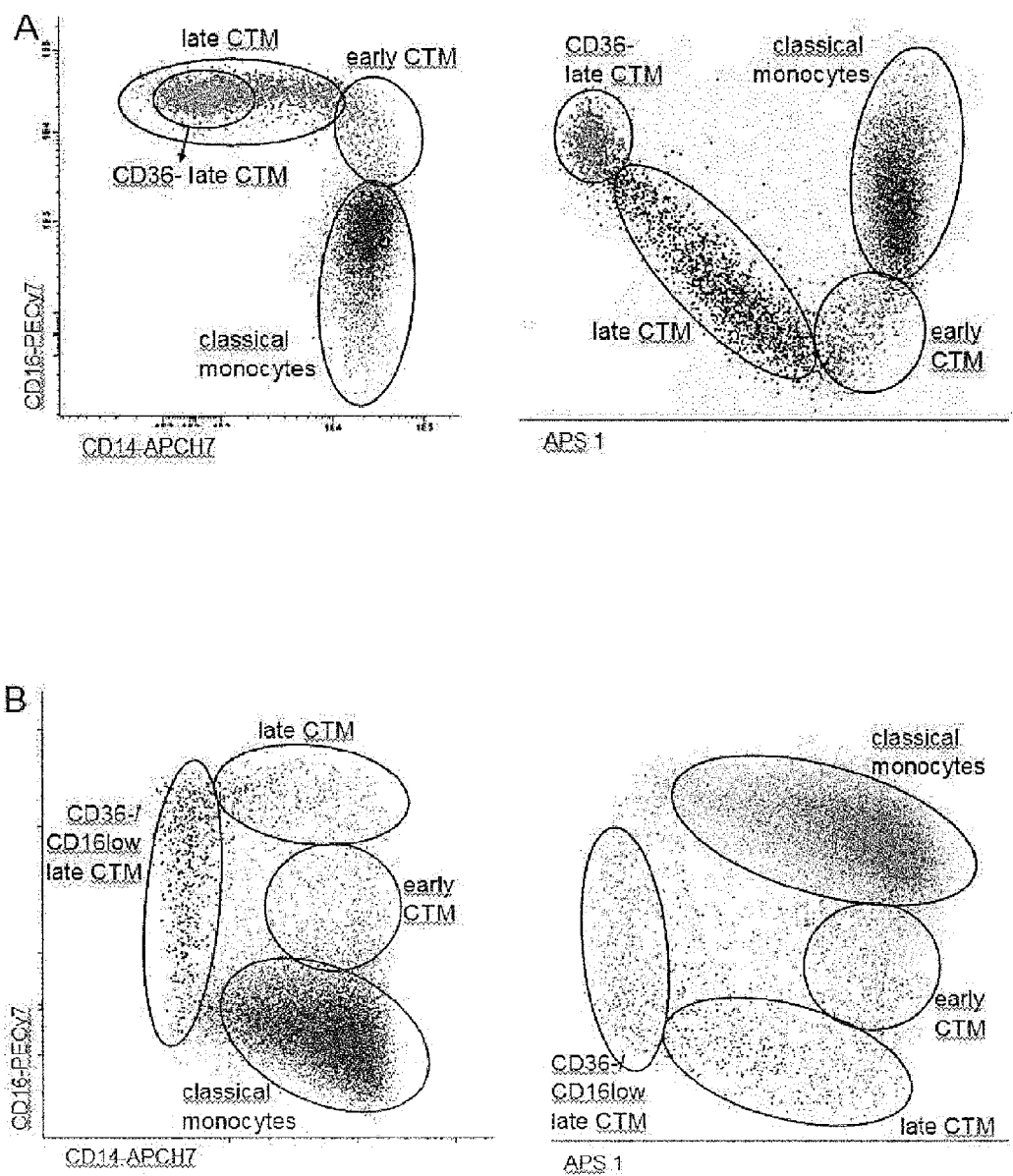

Herewith, also provided is a method comprising the step of further subdividing the selected CTM based on CD14, CD16, CD36 and CD64, preferably comprising the identification of at least one the following CTM subsets: from CD64high/CD36high/CD14high/CD16low to CD64high/CD36high/CD14high/CD16high, CD64high/CD36high/CD14low/CD16high, CD64low/CD36high/CD14−/CD16high and CD64low/CD14−/CD16low/CD36− to low cells (FIG. 4 and FIG. 5).

Any type of biological sample isolated from a mammalian subject, typically a human subject, known or suspected to contain circulating tissue macrophages may be used. For example, the biological test sample comprises peripheral blood, ascitic fluid, pleural effusion, cerebrospinal fluid, bone marrow, lymph node, lymph fluid, synovial fluid, or a single cell suspension prepared from a solid tissue. Peripheral blood is particularly suitable as it can be readily obtained from a subject by a minimally invasive procedure, such as venipuncture.

A method of the invention is advantageously performed in a multi-tube format, which offers the possibility to combine information on CTSM subsets. This is based on the fair assumption that, under normal homeostatic conditions, each individual CTSM can be positive for peptides (protein fragments) from a single tissue only. Hence, also provided is a method wherein two or more aliquots of the same biological test sample are stained in parallel with the same backbone markers for CTM subset identification, but with different additional antibody reagents for more detailed subsetting of individual CTSM populations, according to the tissue origin, based on the detection of protease-induced protein fragments derived from tissue-associated proteins, aiming at scanning of the homeostatic status and the potential disruption of tissue homeostasis in the tissues of the total body.

Herwig et al. (2004, 2005, EP1516182) and Leers et al. (2008) disclosed detection in prostate cancer patients of the presence of circulating CD14het/CD16het tissue macrophages, which they claim to contain intracellular prostate specific antigen (PSA). Leers et al. (2008) conclude that in patients with benign hyperplasia versus localized prostate cancer versus metastasized prostate cancer, the frequency of the PSA positive tissue macrophages in blood is progressively increased (Leers et al, Am J Clin Pathol 2008). However, their presented flow cytometric data seem to contain false-positive results with respect to the PSA staining:

the PSA positive cells are not detectable as a separate population, other than a cut-off from the CTM population via "controlled" marker setting;

the high frequency of seemingly PSA-positive CD14dim/CD16high tissue macrophages are at an unusual position in both the light scatter plot and the CD14 versus CD16 plot, indicative for doublet formation and, consequently, for potential false-positivity for PSA.

Hence, albeit that the increased frequency of CTMs might well be derived from the prostate, the final proof via PSA staining is not convincing. This is most likely caused by insufficient reactivity of the applied anti-PSA antibody against the PSA peptides present in the CTSM population. In this context it should be noted that the applied PSA antibody was selected to recognize intact PSA protein, rather than epitopes on fragments or peptides derived from the intracellular processing and degradation of PSA. Consequently, the original PSA epitope recognized by the PSA antibody is most likely lost in the PSA peptides that were present in the CTSMs, and hence not detectable.

The gating strategies by Herwig et al. (European Urology Suppl., Vol. 5, No. 2, (2006 Apr. 1), page 275, XP005522982; and J. of Urology, Vol. 181, No. 4 (2009 Apr. 1), pg. 653, XP025979386), Leers et al. (2008), Brozek (WO2010/015633), and Japink et al. (Gastroenterology, Elsevier, Vol. 134, no. 4, (2008 Apr. 1), page A-487) are not sufficient for inclusion of all CTMs and not sufficient for exclusion of all non-CTMs. This is mainly caused by the fact the above scientists have chosen for inclusion gating based only on SSC and CD45 or negative selection based on CD19, CD56, CD57 and/or CD161, without confirmation of appropriate exclusion of cell multiplets. Such gating strategies lead to false positive results and might also lead to false negative results.

In contrast to previous work by others (Herwig et al., Leers et al. and Japink et al.) and our own group, here we propose a procedure for identification of all distinct subsets of classical monocytes and CTMs based on an additional positive marker selection (CD300e+ cells and preferably also HLADR+), without a need for exclusion of other cells such as T, NK and B lymphocytes. Such procedure, allows for easy direct exclusion of CD300e− lymphocytes, at the same time it facilitates the identification of late stage CD14−/CD16low CTMs which are usually excluded if selection of CTMs is exclusively based on CD14+ and/or CD16+ cells (FIG. 4 and FIG. 5).

A diagnostic CTM kit without the herein presented inclusion markers and CTM subset markers can not be reliably applied in routine diagnostic practise, where accurate relative and absolute quantitation of cell populations are required.

Step c) of a method provided herein involves the identification of at least one subset of circulating tissue-specific macrophages (CTSM) using one or more detecting antibodies directed against one or more epitopes on at least one protease-induced protein fragments derived from intracellular degradation of a protein by individual CTM in their tissues of origin. The skilled person will understand that according to the concept underlying the invention various approaches can be undertaken. For example, the detecting antibody reagents comprise antibodies for intracellular staining of (FIG. 6):

a) one or more epitopes of a single protease-induced protein fragment derived from an intracellularly processed tissue-associated protein;

b) one or more epitopes of two or more distinct protease-induced protein fragments derived from one intracellularly processed tissue-associated protein;

c) one or more epitopes of two or more distinct protease-induced protein fragments derived from two or more intracellularly processed proteins derived from normal cells from a single organ or tissue;

d) one or more epitopes of two or more distinct protease-induced protein fragments derived from two or more intracellularly processed proteins derived from abnormal cells from a single organ or tissue;

e) one or more epitopes of two or more distinct protease-induced protein fragments derived from two or more intracellularly processed proteins derived from normal and abnormal cells from a single organ or tissue, including a combination of at least one antibody against peptide epitopes of a normal protein and at least one antibody against peptide epitopes from an aberrant protein, and;

f) one or more epitopes of two or more distinct protease-induced protein fragments derived from two or more intracellularly processed proteins derived from normal or abnormal cells from two or more organs or tissues.

In one embodiment, the panel of backbone reagents used for the subsetting of CTM is combined with one or multiple reagents directed against one or more epitopes of two or more distinct protease-induced protein fragments derived from two or more intracellularly processed proteins derived from normal or abnormal cells from two or more organs or tissues. The panel of reagents used for the subsetting of CTM may be combined with one or multiple reagents directed against one or more epitopes of two or more distinct protease-induced protein fragments derived from two or more intracellularly processed proteins from normal and abnormal cells from two or more different organs or tissues, including a combination of at least two reagents each directed against peptide epitopes of different proteins derived from distinct organs or tissues, wherein at least one is an altered tissue.

In one embodiment, the at least one detecting antibody allows for detection of one or more peptide epitopes derived from an aberrant protein, preferably wherein the aberrant protein is selected from the group consisting of oncogenic proteins, mutated proteins, fusion proteins, proteins derived from an allergen and proteins from derived from a pathogen like a virus, a bacterium, a parasite or a fungus.

According to the proteases present in the macrophages and the tissue-specific and disease-specific proteins, it will be possible to predict (at least in part) which peptides will be present in the phagosomes of each CTSM subset. Development of antibodies against the relevant tissue-specific protein fragments or peptides will allow detailed characterization of the circulating tissue macrophages and identification of multiple subsets of different CTSMs. Once the composition of the total CTM and CTSM compartment has been assessed, it will be possible to detect and identify changes in the size and relative composition of the CTM and CTSM populations in relation to changes in e.g. tissue homeostasis, associated with ageing, tissue stress, specific diseases or therapies.

In this way, dissection of the size and composition of the CTM-CTSM compartment provides a mirror of tissue homeostasis and any disruption of tissue homeostasis. Consequently, monitoring over-time will give insight in the occurrence of any homeostatic changes, caused by specific activities, senescence, disease, treatment, etc. Therefore flow cytometric analysis of the CTSM subsets provides a diagnostic tool for evaluation of tissue integrity and/or tissue disruption. Thereby, flow cytometric CTSM subset screening becomes a sensitive method for total body scanning, so-called "Flow cytometric Body Scanning" (FlowBoScan) or "Tissue Macrophage Scan" (TiMaScan).

The FlowBoScan or TiMaScan is most likely more sensitive than classical CT scans or other total body scans and imaging systems, because the CTSM compartment provides a magnified body scan via the collection of "tissue garbage" (apoptotic and dead cells) from all tissues concentrated in single cells with special attention for tissues with disrupted homeostasis such as damage, inflammation, and cancers, etc. Consequently, the CTSM-based scan as disclosed herein will therefore be able to detect tissue damage or diseases in an early stage, both when the defects are diffusely distributed at low level and when they are present as small focal defects. Furthermore, as soon as the diagnosis has been made and treatment has been started, the relevant CTSM subset can be monitored to obtain insight in the effectiveness of the therapy, i.e. the disappearance (or not) of the CTSMs that are related to the disease process.

In parallel to the monitoring of treatment effectiveness, also the toxicity of the provided therapy can be monitored by analyzing CTSM subsets derived from other tissues, which are also more prone to be targeted by the therapy as an unwanted side effect, e.g. hematopoietic cell-associated toxicity of cytotoxic drugs. Consequently, it might even be possible to guide the therapy intensity according to the combined CTSM results. This form of individualized medicine is becoming increasingly important to prevent late sequelae and thereby increase quality of life (Alllison, Nature Biotechnol 2008).

The proposed measurement of disruption in tissue homeostasis in a method according to the invention may at first glance seem to resemble the measurement of serum proteins. However, only a part of the tissue proteins can be detected in the serum (e.g. liver transaminases, PSA and other serine proteases of the kallikrein family, or myoglobin). Moreover, only in case of substantial tissue damage, such as in cardiac infarction or liver damage, these serum proteins show increased levels. Other tissue proteins are not readily detectable in serum, in line with the physiological mechanisms which hide auto-antigens from immune-surveillance via specialized transporting proteins, C-reactive protein (CRP) and other plasma proteins and via tissue protein destruction by local cell proteases and inflammatory or phagocytic cells (e.g. tissue macrophages). Finally, released tissue-specific proteins are diluted in a large volume of tissue fluids (e.g. lymph) and serum throughout the body typically reaching undetectable concentrations in normal homeostasis and early stages of disruption of normal homeostasis.

The herein described system for detection and identification of CTSM subsets is focused on the detection of epitopes on fragments derived from intracellularly processed and digested proteins (e.g. peptides) in single CTSM cells. The system is referred to as "FlowBoScan" or "TiMaScan", which is a flow cytometric body scan via assessment of the relative and absolute frequency of CTMs and CTM subsets and tissue-specific subsets of these CTMs, being the CTSMs and CTSM subsets. The specific power of the described system concerns the possibility to screen the whole CTSM compartment in a blood sample for the origin of the individual CTSM subsets and to define these subsets based on combinations of multiple tissue-specific protein-derived fragments (peptides), including those derived from aberrantly expressed or disease-associated proteins such as oncoproteins, fusion proteins, allergen-derived proteins and microorganism-derived proteins. In this way, the total CTSM compartment reflects (mirrors) the ongoing processes in the various tissues of the total body, whether homeostatic or disturbed.

The target cells in blood include CD16+ tissue macrophages (e.g. CD14het/CD16het CTM) as well as CD14++/CD16− monocytes and different populations of circulating dendritic cells such as myeloid (CD11c+/CD14−/CD16−/HLADR+) and plasmacytoid (CD11c−/CD123++/CD14−/CD16−/HLADR+) dendritic cells, and dendritic cell precursors. CTSM derived from different organs and tissues circulate via the lymph vessel system and blood under normal physiological conditions. Thus, apart from being present in blood they can also be found in their tissues of origin as well as in other associated body fluids such as ascitic fluid, pleural effusions, lymph fluid draining into local or regional lymph nodes, among others. In this invention, we mainly (but not exclusively) focus on the CTSM compartment in the blood.

For the identification and enumeration of CTSM in blood, multiparameter flow cytometry is suitably used. The flow cytometry procedure will aim at simultaneous identification of the total population of CTM in blood samples and their characterization at the single cell level with respect to the intracellular presence of one or more epitopes from one or multiple fragments or peptides from tissue-and/or disease-associated proteins processed by the tissue macrophages at one or multiple organs and tissues (identification of CTSM subsets).

For this purpose a blood sample is stained with a combination of two groups of differentially-labeled antibody markers (see Table 2):

1. A first set of (backbone) markers aimed at the identification and enumeration of different subsets of CTM;
2. A second group of markers devoted to simultaneous intracellular detection of one or more epitopes on protein fragments or peptides derived from the degradation of one or more proteins processed by individual CTMs in their tissues of origin.

The antibodies are provided with a detectable label that allows for their separate detection and quantitation. Detectable (e.g. fluorochrome) labels are known in the art. For example, the panel of differentially-labeled antibody reagents comprises a combination of compatible fluorochromes selected from fluorescein isothiocyanate (FITC), phycoerythrin (PE), peridin chlorophyll protein (PerCP), allophycocyanin (APC), ALEXA FLUOR® 488, ALEXA FLUOR® 647, ALEXA FLUOR® 710, ALEXA FLUOR® 405, cyanin 5 (CY5™) Cyanin 5.5 (Cy5.5), PACIFIC BLUE™ (PacB), BRILLIANT VIOLET® (e.g. BV421), HORIZON VIOLET™ 450 (HV450), PACIFIC ORANGE™ (PacO), HV500, KROME ORANGE™, OC515, quantum dots and conjugates thereof coupled with PE, to APC or to PerCP (e.g. PE/Cy5, PE/Cy5.5, PE/Cy7, PerCP/Cy5.5, APC/Cy7, PE-Texas Red), APCCy750, or any additional compatible fluorochrome or fluorochrome tandem.

In another embodiment, the panel of differentially-labeled antibody reagents comprises a combination of compatible radioisotopes.

TABLE 2

Exemplary procedure for sample preparation
and multicolour staining of CTMs and CTSMs Procedure A. Staining of cell surface
markers of CTMs and CTSMs 1. Add the appropriate volume of antibodies directed against cell surface markers, as recommended for each specific CTM or CTSM antibody panel.
2. If necessary, use PBS + 0.5% of BSA to reach a final volume of 100 µL per tube.
3. Mix well.
4. Incubate for 15 min at room temperature (RT) protected from light.
5. Add 2 mL of 1x FACS Lysing Solution (10x FACS Lysing Solution diluted 1/10 vol/vol in distilled water (dH₂0); Becton Dickinson, San Jose, CA).
6. Mix well.
7. Incubate for 10 min at RT protected from light.
8. Centrifuge for 5 min at 540 g.
9. Discard the supernatant using a Pasteur pipette or vacuum system without disturbing the cell pellet, leaving approximately 50 µL residual volume in each tube.
10. Add 2 mL of PBS + 0.5% of BSA to the cell pellet.
11. Mix well.
12. Centrifuge for 5 min at 540 g.
13. Discard the supernatant using a Pasteur pipette or vacuum system without disturbing the cell pellet, leaving approximately 50 µL residual volume in each tube.
14. Resuspend the cell pellet in 200 µL PBS + 0.5% of BSA.
15. Acquire the cells after staining or (if not immediately acquired) store at 4° C. maximally for 3 hours until measured in the multicolor flow cytometer Procedure B. Combined staining of cell
surface membrane and intracellular
markers of CTMs and CTSMs 16. Continued from Procedure A step 13.
17. Add the appropriate volumes of antibodies, as recommended for each specific CTM or CTSM antibody panel.
18. If necessary, use PBS + 0.5% BSA to reach a volume of 100 µL per tube.
19. Mix well.
20. Incubate for 15 min at RT protected from light.
21. Add 2 mL of PBS + 0.5% of BSA to the cell pellet.
22. Mix well.
23. Centrifuge for 5 min at 540 g.
24. Discard the supernatant using a Pasteur pipette or vacuum system without disturbing the cell pellet, leaving approximately 50 L residual volume in each tube.
25. Resuspend the cell pellet by mixing gently.
26. Add 100 µL of Reagent A (fixative; Fix&Perm ™, An der Grub, Vienna, Austria)*
27. Incubate for 15 min at RT protected from light.
28. Add 2 mL of PBS + 0.5% of BSA to the cell pellet.
29. Mix well.
30. Centrifuge for 5 min at 540 g.
31. Discard the supernatant using a Pasteur pipette or vacuum system without disturbing the cell pellet, leaving approximately 50 µL residual volume in each tube.
32. Resuspend the cell pellet by mixing gently.
33. Add 100 µL of Reagent B (permeabilizing solution; Fix&Perm ™)*

TABLE 2-continued

Exemplary procedure for sample preparation
and multicolour staining of CTMs and CTSMs 34. Mix well.
35. Add the appropriate volume of the antibodies against the intracellular peptides (protein fragments).
36. Mix well.
37. Incubate for 15 min at RT protected from light.
38. Add 2 mL of PBS + 0.5% of BSA to the cell pellet.
39. Mix well.
40. Centrifuge for 5 min at 540 g.
41. Discard the supernatant using a Pasteur pipette or vacuum system without disturbing the cell pellet, leaving approximately 50 µL residual volume in each tube.
42. Resuspend the cell pellet in 200 µL PBS + 0.5% of BSA.
43. Acquire the cells after staining or (if not immediately acquired) store at 4° C. maximally for 3 hours until measured in the multicolor flow cytometer.

*Also other methods for fixation and permeabilization might be used, e.g. FACS Lysing Solution.

A minimum of 3, preferably 4, backbone markers is required for the identification of the CTMs. This set of backbone markers contains at least CD14, CD16 and CD300e and preferably also HLADR. Further useful markers include CD11c, CD33, CD36, CD45 and/or CD64 cell surface leukocyte antigens (e.g. CD14/CD16, CD11c/CD16, CD33/CD16, CD64/CD16, CD11c/CD14/CD16, CD33/CD14/CD16, CD33/CD11c/CD16, CD300e/CD14/CD16, CD300e/HLADR/CD14/CD16, CD300e/HLADR/CD64/CD16/CD14, CD300e/CD11c/CD16/CD64, CD300e/HLADR/CD64/CD36/CD16/CD14 or marker combinations of these markers to which CD45 is added). Generally, the subtle differences in the expression of a single cell surface marker (or even two markers) might not always be sufficient for the accurate recognition of all CTM's and CTM subsets (FIG. 2C), but when the overall profile of multiple markers is assessed by multivariate analysis such as principal component analysis (PCA), e.g. using automated population separation—APS view—in Infinicyt software, or multidimensional scaling (MDS) analysis the CTM's and CTM subsets can be identified more accurately (FIG. 3). In the example shown in FIG. 3, in the APS1 and APS2 views bidimensional representations of the first versus the second principal components and of the third versus the fourth principal components are displayed for CD14het/CD16het cells stained for CD14, CD16 and other multiple backbone markers. The most powerful combinations of parameters to discriminate between the classical monocytes and the CTMs are used by decreasing value in principal components 1, 2, 3 and 4, respectively.

Hence, the invention also provides a method for determining the health status of a subject, for early detection of tissue damage, for early diagnosis and monitoring of a disease, and/or for evaluation of treatment effectiveness in a subject using circulating tissue macrophages (CTM) as a mirror of disrupted tissue homeostasis and disease, the method comprising the steps of:
  a) Providing a biological test sample from the subject which contains circulating tissue macrophages (CTM);
  b) staining said CTM with a panel of differentially-labeled distinct antibodies against the backbone markers CD14, CD16, CD300e and preferably also HLADR, CD64 and CD36 for the identification and enumeration of different CTM subsets (FIGS. 4 and 5);
  c) multiparameter flow-cytometric analysis of said stained CTM to determine the amount of signals of each distinct labeled antibody associated with individual cells, wherein said analysis involves multivariate analysis, preferably principal component analysis (PCA), e.g. using automated population separation—APS view—in Infinicyt software, or multidimensional scaling (MDS) analysis (FIGS. 4 and 5);

d) determining the relative and absolute number of individual cells within each CTM subset;

e) calculating (i) the relative and absolute number of cells within each CTM subset, and;

comparing the test CTM staining profile with a normal CTM staining profile for each tissue evaluated, wherein an aberrant test staining profile is indicative of tissue damage, an altered tissue homeostasis, the presence of a disease, and/or treatment effectiveness versus resistance.

PCA is a mathematical procedure that uses an orthogonal transformation to convert a set of observations of possibly correlated variables into a set of values of uncorrelated variables called principal components. The number of principal components is less than or equal to the number of original variables. This transformation is defined in such a way that the first principal component has as high a variance as possible (that is, accounts for as much of the variability in the data as possible), and each succeeding component in turn has the highest variance possible under the constraint that it be orthogonal to (uncorrelated with) the preceding components. Principal components are guaranteed to be independent only if the data set is jointly normally distributed. PCA is sensitive to the relative scaling of the original variables. Depending on the field of application, it is also named the discrete Karhunen-Loève transform (KLT), the Hotelling transform or proper orthogonal decomposition (POD). Alternatively to PCA, MDS or any other type of well-established multivariate analysis, can be used.

In a preferred embodiment, the evaluation of the above described stainings comprises ≥4-color flow cytometry and, in the more preferred embodiment, ≥5-color flow cytometry approaches, wherein ≥1 of the markers used (colors) corresponds to markers that identify intracellular epitopes on fragments or peptides derived from the degradation of one or multiple tissue-and/or disease-associated proteins which had been captured locally at their tissue of origin and processed by the CTM, and where the other markers are backbone markers, respectively.

In addition to the above listed backbone markers, other markers can be used for specific exclusion of other non-CTM cell populations, e.g. CD15 and/or CD24 may be used to exclude neutrophils, CD56 and/or CD7 to exclude NK-cells, CD3 for T-lymphocytes, CD19 and/or CD20 for B-cells and CD123 for plasmacytoid dendritic cells.

Staining of CTMs and other cell populations in the sample, includes staining for both cell surface membrane markers as well as intracellular markers using conventional direct immunofluorescence techniques combined with different well described cell fixation, cell permeabilization and erythrocyte lysing procedures and reagents (see Table 2).

Noteworthy, for an individual peripheral blood sample, the number of protein fragments or peptide epitopes from one or multiple tissue-and/or disease-associated proteins processed by the CTM, might be greater than allowed to be measured in combination with the selected backbone markers, due to the limited multicolor analytical capabilities of the flow cytometer used. In such case, multiple aliquots of the same peripheral blood sample are required, which are each stained for the same set of backbone markers and for a different (partially overlapping or not) panel of epitopes from one or multiple tissue-and/or disease-associated proteins processed by the CTM's.

After measured in the flow cytometer using conventional data acquisition procedures, in such case the merge and calculation tools of the Infinicyt software (Cytognos SL, Salamanca, Spain) are advantageously used to create a single data file that contains all protein fragments-associated epitope measurements for individual cells contained in the populations of CTM present in the sample. For the identification of the CTM cells and their (sub)populations of interest, multidimensional gating strategies such as those implemented in the Infinicyt software, based on sequential Boolean gating, principal component analysis and multidimensional scaling, may be used on the basis of the backbone markers and the characterization markers, respectively. Useful gating strategies are described herein above.

In addition, conventional procedures to evaluate absolute cell counts of the overall CTM population and their distinct subpopulations identified per unit of sample volume may be used in parallel to calculate the exact number of cells per unit of sample volume. Such procedures may use volumetric approaches or commercially available internal reference beads such as TrueCOUNT (Becton Dickinson Biosciences, San José Calif., USA), FlowCOUNT (Beckman Coulter, Miami, Fla., USA) or PerfectCOUNT (Cytognos SL) beads.

The skilled person will understand and appreciate that the present invention involving flow cytometric studies on CTM analysis can be used for (early detection of) various diseases, disorders or other physiological changes and abnormalities. Provided herein are diagnostic kits comprising the reagents for performing an analysis based on the concept disclosed herein.

The diagnostic kit may comprise in a first container a set of backbone markers comprising differentially-labeled antibodies aimed at the identification and enumeration of at least two, preferably at least three, different subsets of CD14high/CD16+, CD14high/CD16high, CD14+/CD16high, CD14low/CD16high CD14−/CD16high, CD14−/CD16low, CD11c+/CD16+, CD11c+/CD16high, CD11c+/CD16low, CD33high/CD16+, CD33high/CD16high, CD33+/CD16high, CD33+/CD16low, CD300e+/CD16+, CD300e+/CD16++ and CD300e+/CD16low CTM subsets. Provided is a diagnostic kit comprising in a first container a set of backbone markers comprising differentially-labeled antibodies, wherein the backbone markers are CD300e, CD14 and CD16 and preferably also HLADR. The kit optionally instructions for use of the kit for identification and enumeration of at least one, preferably at least two, more preferably at least three, CTM subsets, preferably according to a method disclosed herein.

The first container comprises antibodies directed at markers CD14, CD16 and CD300e, preferably CD14, CD16, CD300e and HLA-DR. More preferably, at least one additional antibody is present which selected from the group of antibodies directed at marker CD36, CD64 or CD45. For example, at least a set of antibodies directed at CD14, CD16, CD300e, HLADR and CD45 is used, optionally in combination with an anti-CD64 antibody. In a specific aspect, the first container comprises antibodies directed at markers CD14, CD16, CD300e, HLADR, CD64 and CD36.

In a preferred embodiment, a diagnostic kit comprises in a first container a set of backbone markers comprising differentially-labeled antibodies aimed at the identification and enumeration of at least one, preferably at least two, more preferably at least three, CTM subsets, wherein the backbone markers are CD14, CD16, and CD300e and preferably also HLADR. In a specifically preferred aspect, the invention provides a kit comprising a combination of antibodies against CD14, CD16, CD300e, HLADR, CD45, CD64 and CD36 (FIG. 4), wherein each of the antibodies is conjugated to a distinct detectable label. For example, the kit comprises a CD14-antibody conjugated to fluorochrome 1 (FL1), a CD16-antibody conjugated to fluorochrome 2 (FL2), a CD300e-antibody conjugated to fluorochrome 3 (FL3), a HLADR-antibody conjugated to fluorochrome 4 (FL4), a CD45-antibody conjugated to fluorochrome 5 (FL5), a CD64-antibody conjugated to fluorochrome 6 (FL6), and a CD36-antibody conjugated to fluorochrome 7 (FL7). The skilled person will understand that any useful combination of fluorochromes can be used. For instance, the kit comprises the fluorochrome combination APCH7 (e.g. antiCD14-APCH7), PECy7 (e.g. anti-CD16-PECy7), APC (e.g. anti-CD300e-APC), PacB (e.g. anti-HLADR-PacB), FITC (e.g. anti-CD36-FITC) and PE (e.g. anti-CD64-PE).

For the identification of tissue-specific circulating macrophages, the kit may contain in a second container at least one labeled detecting antibody allowing for detection of one or more epitopes on at least one protease-induced protein fragment derived from intracellular degradation of a protein by individual CTM in their tissues of origin.

Figure 7:
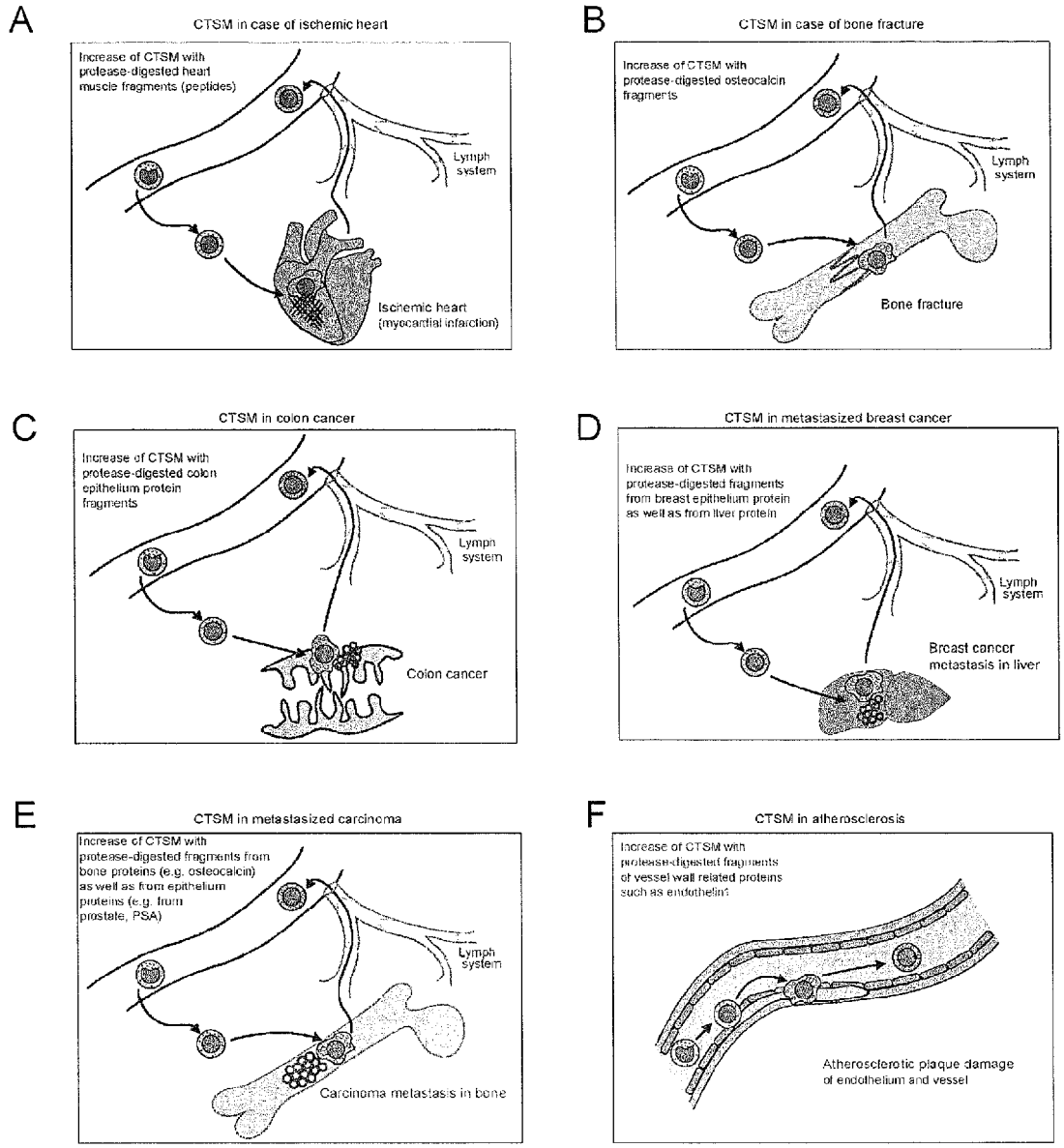
Figure 7:
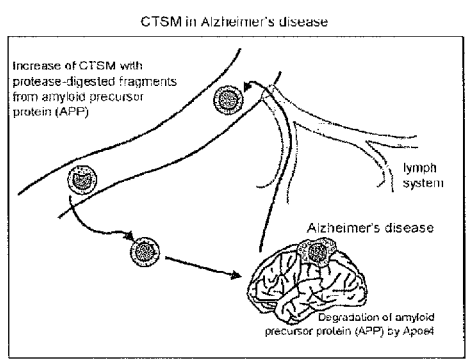
Figure 7:
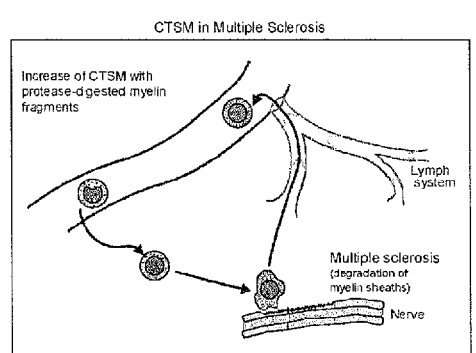
Figure 7:
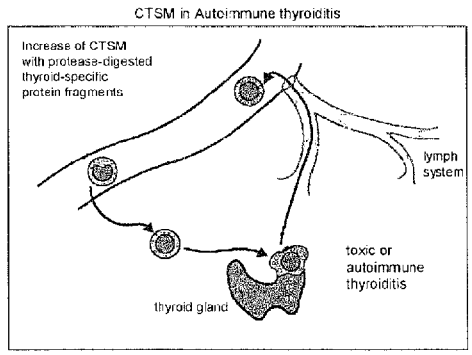
Figure 7:
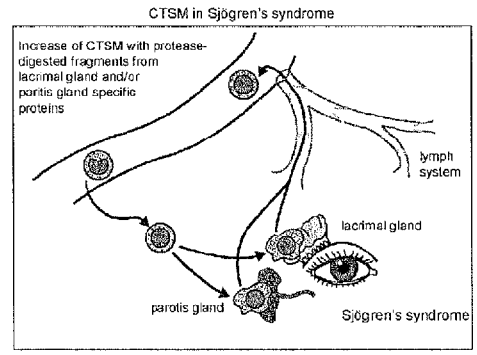
Figure 7:
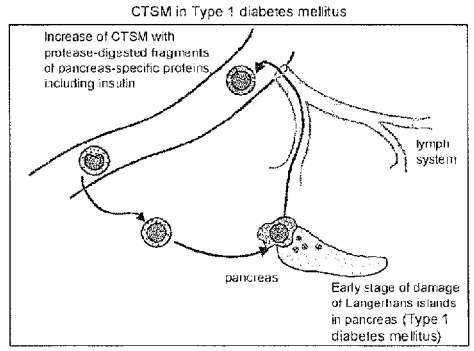
Figure 7:
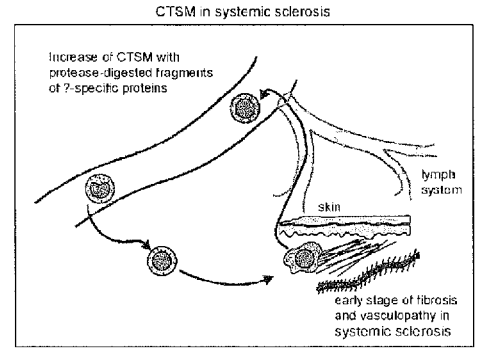
Figure 7:
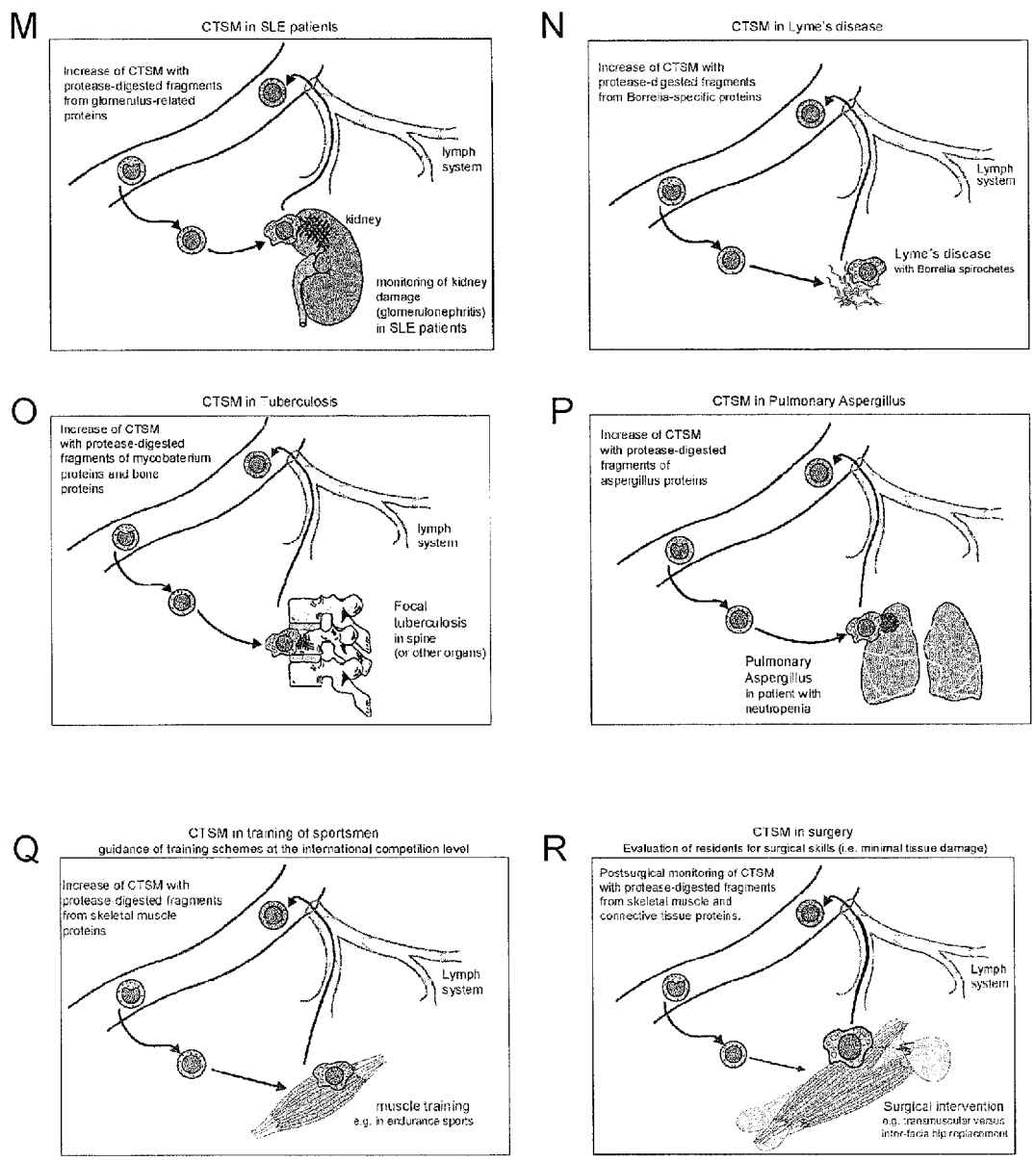

As will be understood, the target(s) of detecting antibodie(s) can be selected according to the specific condition or disease of interest. Useful (fluorochrome-conjugated) antibodies are commercially available. FIG. 7 shows merely an arbitrary set of different applications, each requiring different detecting antibodies. WO2010/015633 (herein incorporated by reference) discloses in claim 9 a list of targets for useful antibodies.

Useful considerations for selecting a detecting antibody target include the following. The antigen is preferably not a secreted protein, such as PSA, CEA, etc., because of the possibility that high serum levels of this protein give a diffuse "background" in or on CTM subsets. In addition, the tissue-specific protein should preferably also be expressed on immature cells of the same tissue. Still further, the selected protein domains/epitopes should preferably not occur elsewhere in the "proteome", i.e. in other proteins.

Another relevant factor to take into account is the fact that most tissues will give a normal background of tissue-marker positive CTMs in the blood, because of the homeostatic activity level between cell proliferation and apoptosis. However, some external epithelial layers will most likely not give this "normal background". For example, in a healthy individual the continuously renewed gut epithelium will mostly be shed into the lumen of the gut, implying that virtually no CTMs with gut-specific protein fragments are expected to be present in blood. However, if the gut epithelial cells transform into malignant invasive cells, local CTMs will phagocytose apoptotic malignant cells and will become detectable in blood as CTSM with gut (e.g. colon) specific protein fragments. Detection of (increased) circulating CTSM with colon-specific protein fragments can be used for nation-wide screening programs for early detection of colon cancer. The same is most likely valid for lung epithelial cells, which will be shed into the alveoli and bronchi and will most likely be phagocytozed by alveolar macrophages that will be removed from our body via the bronchi (mucus removed via cilia movements to the sputum). However, invasive epithelial cells (as in lung cancer) will result in lung-epithelium positive CTSM in blood. Finally, a comparable process will take place for the skin, where normal melanocytes will be lost from the skin surface, which is in contrast to melanoma cells, which become invasive by passing the basal membrane. Only under such circumstances, is might be possible to detect Melan-A-positive CTSM in blood on top of the low background of Melan-A-positive cells derived from the retina.

A very important additional application of a method or kit according to the invention is the detection of non-self (i.e. exogenous) protein-fragments, such as in case of insidious infections diseases. Particularly in case of insidious infectious diseases, which are very difficult to diagnose. For example, it is very difficult to diagnose (extra-pulmonary) tuberculosis, because all currently used serological and PCR tests show high levels of false results. Detection of *Mycobacterium*-specific protein fragments in blood CTM subsets provides an excellent alternative and potentially far more reliable diagnostic tool also to evaluate disease dissemination throughout the body. The same is valid for diseases caused by other pathogens such as Aspergillosis, Lyme disease, and Q fever.

In one specific embodiment, the invention provides a diagnostic kit wherein the second container comprises at least one detecting antibody allowing for detection of one or more epitopes derived from intracellular degradation of heart muscle specific proteins (e.g. troponine or CK-MB), kidney/glomerulus-specific proteins, liver-specific proteins, or lung-specific proteins, aiming at the assessment of post-transplant organ survival and transplant rejection processes in patients with heart, kidney, liver, or lung transplantation, respectively.

In a second embodiment, a diagnostic kit wherein the second container comprises at least one detecting antibody allowing for detection of one or more epitopes derived from intracellular degradation of heart muscle specific proteins provides the means and methods for detecting angina pectoris or extensive ischemia of the heart (with cardiac infarction). End-stage TSM from the damaged heart muscle migrate via the lymph vessel system to the blood, where they can be detected in relatively and absolutely high numbers as CTSM, containing protein fragments derived from heart muscle specific proteins (FIG. 7A) Such analysis might be useful for making an early diagnosis in progressive angina pectoris and/or for monitoring the extent and repair of a myocardial infarction.

In another embodiment, the second container in a kit of the invention comprises at least one detecting antibody allowing for detection of one or more epitopes derived from intracellular degradation of bone proteins, such as osteocalcin, osteopontin or bone-specific alkaline phosphatase, allowing for assessing the complexity and extent of bone fractures and at assessing the progression of bone remodelling after bone fractures and surgical interventions. For example, monitoring of bone remodeling can be achieved, for example in patients with complex bone fractures. Regular enumeration of CTSM that contain fragments from bone-specific proteins (e.g. osteocalcin, osteopontin and/or bone alkaline phosphatase peptides) allow such monitoring (FIG. 7B).

In another embodiment, the invention provides a kit, e.g. for early diagnosis and monitoring of malignancies, wherein the second container comprises at least one detecting antibody against one or more protease-induced protein fragments derived from intracellular degradation of an epithelium protein, preferably a breast epithelium protein, an esophagus epithelium protein, a gastric epithelium protein, a pancreas epithelium protein, a colon epithelium protein, a rectum-sigmoid epithelium protein, a thyroid epithelium protein, a lung or bronchus epithelium protein, a prostate epithelium protein, a bladder epithelium protein, a cervix epithelium protein, an uterus epithelium protein, melanoma protein kidney-glomerulus protein, or against another epithelial cell marker. Early diagnosis and monitoring of invasive colon cancer can be achieved via detection of CTSM in blood which contain colon epithelium-specific protein fragments (FIG. 7C). Such application is particularly valuable in patients with familial polyposis coli, because regular monitoring (e.g. yearly or 6-monthly) might allow early diagnosis of progression of polyposis coli into invasive colon cancer.

In a fifth embodiment, the invention provides a means and methods for early detection of metastasis of breast carcinoma in the liver. Screening of breast carcinoma patients for metastases in liver (or in other organs, such as bone and lung) will be possible by searching for CTSM that simultaneously contain protein fragments derived from both breast epithelial proteins and from liver-specific proteins (FIG. 7D). The combined presence of the two different types of protein fragments from two completely different tissues in one individual CTSM, points to the presence of a metastasis, for example metastasis to liver, bone, lung or central nervous system (CNS). In one embodiment, a method of the invention comprises the combined detection of tissue-specific protein fragments from liver or bone as well as from carcinoma cells as measure for liver or bone metastases of breast carcinoma, prostate carcinoma, etc.

Progressive and invasive prostate cancer needs to be detected in an early stage. The invention provides means and methods for screening of prostate cancer patients for the presence of CTSM that contain peptides derived from both prostate epithelial proteins and from bone-specific proteins (FIG. 7E) or other types of proteins, e.g. liver, lung, and CNS. Comparable approaches for detection and monitoring of metastases are possible for all types of cancers.

Another embodiment relates to atherosclerosis, where tissue macrophages penetrate the atherosclerotic plaques and most likely directly return to the blood vessel as soon as their tasks are completed. Such CTSM will contain protein fragments from endothelial proteins, such as endothelin 1 (FIG. 7F). A diagnostic kit for use in such analysis (e.g. aiming at the assessment of atherosclerosis and the extent of endothelial damage in patients with atherosclerosis) may hence comprise at least one detecting antibody allowing for detection of one or more epitopes derived from intracellular degradation of endothelial proteins (e.g. endothelin 1).

A further embodiment relates to methods and kits for early diagnosis and monitoring of brain or nerve disease, in particular Alzheimer, wherein at least one detecting antibody allows for detection of one or more epitopes derived from intracellular degradation of brain or nerve specific proteins, for example Apoε4 or, amyloid precursor protein (APP). The diagnosis of Alzheimer is frequently delayed and difficult to confirm. Also monitoring of disease progression is complicated. Consequently an independent diagnostic assay of the invention can support the care of Alzheimer patients and their families, e.g. for early supportive treatment as well as for in-time financial management. This can be achieved via the detection of increased or increasing CTSM, which contain fragments or peptides derived from Apoε4-digested APP and/or other central nervous system (CNS) tissue- and disease-associated proteins (FIG. 7G). Elevated numbers of APP-peptide positive CTSM could point to early stage Alzheimer and further increase of such APP positive CTSM might point to disease progression.

A kit comprising at least one detecting antibody allowing for detection of one or more epitopes derived from intracellular degradation of brain specific proteins also finds it use in early diagnosis of cerebrovascular accidents (CVA's), e.g. in patients with recurrent transient ischemic attacks (TIA's) and in the subsequent monitoring of the extent and recovery of brain infarction.

Another embodiment relates to Multiple Sclerosis (MS). The diagnosis of MS is complex and would profit from an independent diagnostic assay, which can also be used for monitoring disease progression. This can be achieved using a method provided herein involving precise detection of the relative and absolute frequencies of CTSM containing myelin-specific peptides, derived from degradation of the myelin sheaths that cover the nerves (FIG. 7H).

A diagnostic kit is provided suitable for early diagnosis and confirmation of autoimmune diseases and monitoring of autoimmune diseases, such as aplastic anemia, diabetes mellitus type I, thyroiditis, autoimmune cystitis, Sjögren syndrome, autoimmune glomerulonephritis, rheumatoid arthritis, systemic sclerosis, and other autoimmune connective tissue diseases. Such a kit may comprise in the second container at least one detecting antibody allowing for detection of one or more epitopes derived from intracellular degradation of a protein selected from the group consisting of intrinsic factor, islet of Langerhans specific proteins or insulin, thyroid epithelium proteins, bladder epithelium proteins, lacrimal gland and/or salivary gland specific proteins, kidney-glomerulus specific proteins, synovial membrane specific proteins, muscle and connective tissue specific proteins, For example, early diagnosis or confirmation of toxic or autoimmune thyroiditis can be possible by detection of the relative and absolute frequencies of CTSM, which contain protein fragments derived from thyroid tissue specific proteins (FIG. 7I).

The diagnosis of Sjögren syndrome is difficult and is generally made after substantial delay, also because of the complex differential diagnosis. Increased counts of CTSMs containing fragments from parotis gland or lacrimal gland proteins can significantly support the diagnostic process (FIG. 7J).

Young children from a family with frequent development of Diabetes Mellitus Type 1, can be monitored for the presence of CTSM that contain fragments or peptides from Langerhans islets or other specific proteins, such as insulin (FIG. 7K). Such screening will allow early diagnosis before overt diabetes has developed, thereby allowing early intervention with immunomodulation or immune suppression.

Also in patients with systemic sclerosis, the diagnosis can not always be made easily. Therefore the CTM system might be used for early detection of fibrosis and vasculopathy via the presence of fragments from connective tissue proteins and endothelial cell proteins (FIG. 7L).

Patients with systemic lupus erythematosus (SLE) frequently develop progressive glomerulophritis, finally resulting in irreversible kidney failure. Such kidney damage is generally discovered at a late stage when most kidney function has already been lost and consequently does not allow anymore an immunosuppressive treatment. Therefore we propose that all SLE patients will be monitored regularly for the presence and increase of CTSM, which contain fragments from kidney-specific proteins (FIG. 7M). Early diagnosis of kidney damage (far before increased creatinine levels are found) will allow early intervention with immunomodulation or other immunosuppressive treatment.

A further embodiment relates to diseases caused by (infection with) micro-organisms such as Lyme's disease. The diagnosis of Lyme's disease is frequently complex due to a non-typical clinical picture and/or the absence of classical symptoms such as the tick-bite related skin lesions. Delayed diagnosis of complications in patients with Lyme's disease can lead to irreversible organ damage. Consequently, it is clinically relevant to have an independent diagnostic assay available for the diagnosis of Lyme's disease. This can be achieved via the detection of CTSM, which contain peptides from *Borrelia*-specific proteins (FIG. 7N). Preferably, the selected epitopes for antibody raising should be independent of the *Borrelia* strain, so that each type of *Borrelia* infection can be detected with a single assay. Otherwise multiple antibodies against peptides from several different types of *Borrelia*-strains may be used to identify the involved *Borrelia* strain that caused the Lyme's disease in a specific patient.

Conventional diagnostic tests for tuberculosis have several limitations, particularly in case of extrapulmonary tuberculosis. Several antibody-based serum assays have been developed, but all of them miss at least in part the extrapulmonary diagnosis. However, the detection of CTSM, containing fragments of *Mycobacterium tuberculosis* can contribute to the accurate diagnosis of extrapulmonary Tuberculosis (FIG. 7O).

Patients with granulopenia are highly susceptible to aspergillosis. The earlier the diagnosis of aspergillosis, the better the outcome of the disease. Consequently, it might be wise to monitor all patients with granulopenia for the presence (and increase) of CTSM that contain fragments from *aspergillus*, independent of the involved strain (FIG. 7P).

Hence, also provided is a diagnostic kit wherein the second container comprises at least one detecting antibody allowing for detection of one or more epitopes derived from intracellular degradation of proteins from a pathogen like a virus, a bacterium, a fungus, such as Hepatitis virus, *Borrelia*, *Mycobacterium*, or *Aspergillus* for early detection (or confirmation of the diagnosis) and monitoring of Hepatitis, Lyme disease, tuberculosis, lepra or aspergillosis. In a specific aspect, the diagnostic kit is aimed at the early diagnosis and monitoring of bone localization of tuberculosis, and aspergillosis, and comprises in the second container at least one detecting antibody allowing for detection of one or more epitopes derived from intracellular degradation of bone proteins as well as at least one detecting antibody allowing for detection of one or more epitopes derived from intracellular degradation of a protein from a *Mycobacterium* or *Aspergillus*.

The invention also finds its use in monitoring training of sportsmen in their endurance training, more specifically to determine whether an individual is undertrained or overtrained. Endurance sports need careful training programs for reaching the correct training status at the right moment in competition. The optimal training frequency and intensity might differ significantly between individuals and might be dependent on physical, environmental, and genetic (race) factors, which are currently unknown. Also, recuperation after high level physical exercise might be different between individual sportsmen. Guiding the training and recuperation of sportsmen in endurance sports might be supported by careful monitoring of the CTSM compartment, which is positive for peptides derived from skeletal proteins (FIG. 7Q). This could lead to better guiding of sportsmen in their training schedules in order to prevent both overtraining and undertraining and might result in a significant improvement of individual sports results.

A further embodiment relates to the evaluation of tissue damage, for example to assess the surgical skills of residents in surgery or to evaluate two or more different surgical procedures for the same medical indication. Detection and enumeration of CTMs or CTSMs (with peptides from skeletal muscle or connective tissue, e.g. collagen derived peptides) can serve such evaluation (FIG. 7R). Provided is a diagnostic kit wherein the second container comprises at least one detecting antibody allowing for detection of one or more epitopes derived from intracellular degradation of skeletal muscle. Such a kit finds its use in monitoring and guiding the training and recovery of sportsmen in (international) sports events, such as in endurance sports (e.g. marathon, triathlon, skating, swimming, cycling, langlaufen).

In still a further embodiment, the invention can be used to provide a Personal CTSM profile assessment for Health Status. The subset distribution of CTSM is most likely slightly different between individuals, because such composition is dependent on age and other parameters, such life style habits (e.g. smoking and alcohol usage) as well as activities such as sports. A regular (e.g. yearly or 6-monthly) monitoring of individuals can give good insight in the health status and allows for early detection and diagnosis of disease. The invention allows for the design of personalized CTSM profiles which can be used to screen for specific risks and hazards, such as:

Professional exposure (industrial toxins, etc.);
Life style habits (smoking, eating, drinking, etc.);
Family-associated diseases (cardiovascular, cancer, Alzheimer, etc.)

Per individual a specific personalized combination of tissue-derived peptides can be monitored, aiming at prevention and/or early diagnosis.

LEGEND TO THE FIGURES

FIG. 1. CD16$^+$ tissue macrophages in blood are not directly derived from classical CD14$^{++}$/CD16$^-$ monocytes, but from tissue macrophages, which have actively contributed to surveillance and phagocytosis in tissues, and which have recirculated via the lymph vessel system to the blood stream (Van Dongen and Orfao, unpublished data).

FIG. 2. Several types of monocyte/macrophage subsets can be detected by accurate flow cytometric gating strategies, followed by analysis of CD14 and CD16 staining patterns. A. In a healthy donor the classical monocytes are CD14$^+$/CD16$^-$, while the CTM population exhibits heterogeneous (het) expression of CD14 and CD16, indicating that this population consists of several subsets. B. In patients with an infectious disease (e.g. *Francisella tularensis*), the CD14$^{het}$/CD16$^{het}$ subsets are relatively and absolutely increased. C. Several CTM subsets can be identified in the CD14-CD16 dot plot of the patient with the *Francisella tularensis* infection (A. Orfao et al., unpublished results).

FIG. 3. Precise discrimination between CD14$^{high}$/CD16$^-$ classical monocytes and the more heterogeneous CTMs can be improved by principal component analysis (APS view via Infinicyt software; Cytognos, Salamanca, ES) of all evaluated markers, such as CD14, CD16, CD33, CD45, CD64, CD123, CD300e and HLADR. A. the CD14/CD16 dotplot and CD14/CD123 dotplot suggest that the classical monocytes and CTM represent a continuum. B. The principal component analysis of all 8 markers in APS 1 show that the classical monocytes and CTM are separate populations. In APS 2 view, the two populations appear closely related.

FIG. 4. Staining for expression of CD14, CD16, CD36, CD45, CD64, CD300e and HLADR on blood leukocytes results in a highly accurate recognition of classical monocytes and at least three CTM subsets: early CTM, late CD36+ CTM subsets, and a late CD36– CTM subset. In the presented staining, first gating on intermediate SSC and CD45 is performed (Panel A), followed by inclusion gating based on positivity for CD300e and HLADR (Panel B). The included cells represent all classical monocytes and all CTM, which can further be evaluated with the CD14 and CD16 markers (Panel C), resulting in three main subsets: classical monocytes, early CTM, and late CTM (Panel D). Accurate recognition of the early CTM and further subsetting of the CTMs is possible with CD64 and CD36 (Panels E and F). CD64 is expressed at higher levels on early CTM (and on classical monocytes), whereas all other CTM subsets express CD64 at lower levels (Panel F). The CD64 low CTM (late CTM) have a heterogeneous CD36 expression from high to negative (Panel E and F). The APS view with all seven markers evaluated shows a clear separation of the various monocyte/macrophage cell populations (Panel G), i.e. the classical monocytes, early CTM, late CTM subsets, including the CD36– late CTM subset (Panel H).

FIG. 5. The staining for CD14, CD16, CD36, CD45, CD64, CD300e and HLADR on blood leukocytes results in an accurate recognition of classical monocytes and CTM subsets. These monocyte and CTM subsets might differ in their composition dependent on age (childhood, adolescence, adult, elderly), type of disease (local, systemic, etc.), disease stage (acute, chronic, smoldering, etc.). Panel A shows a pattern of CD300e/HLADR cell populations typically found in adults. In contrast, the blood sample of a sick child in panel B exhibits a different pattern with the prominent presence of a CD16low/CD14–/CD36–/CD64low CTM population, which is small or absent in adult blood. Of note: most CD36– late CTM in adult blood express CD16 at high levels.

Figure 6:
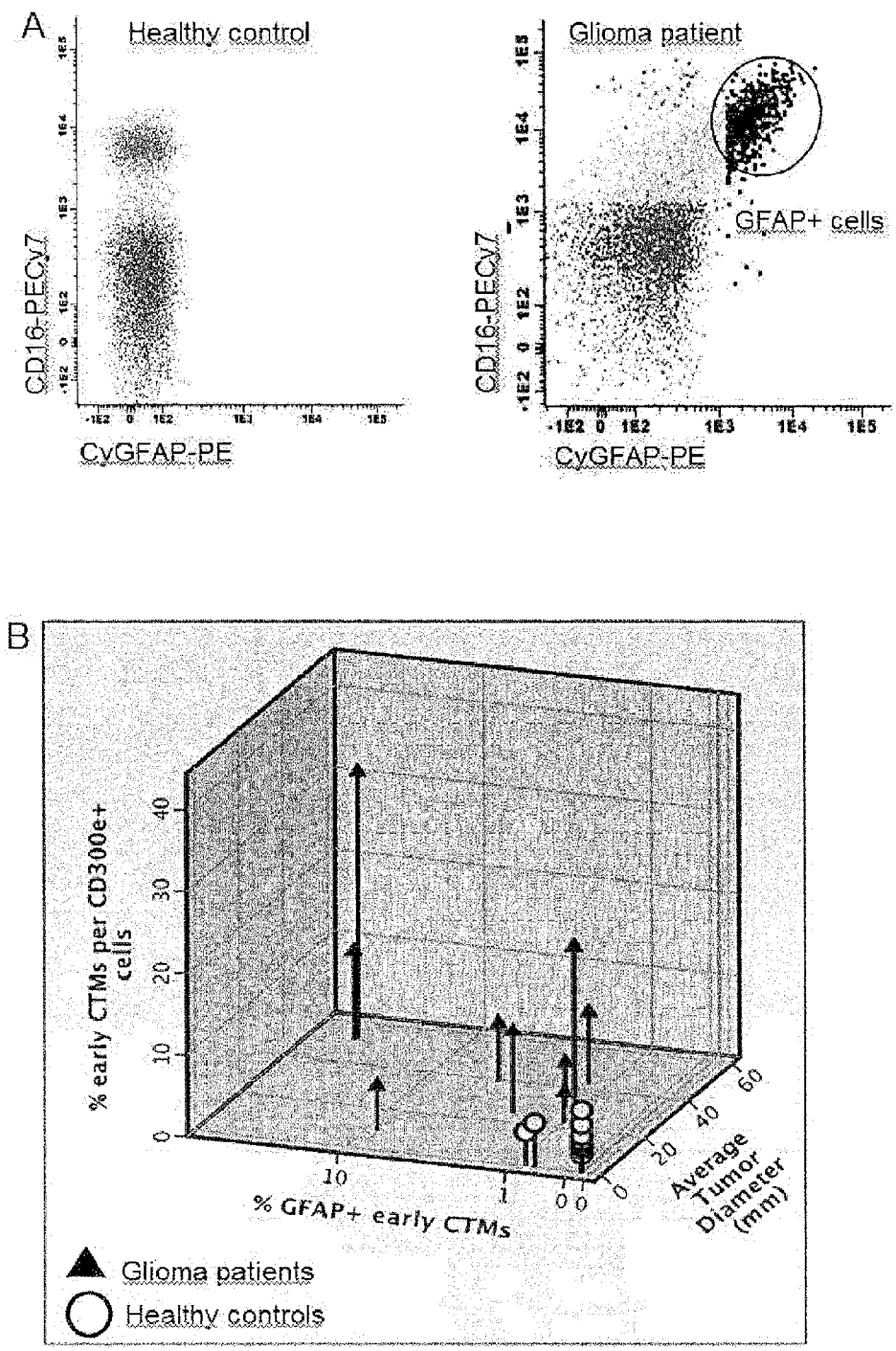

FIG. 6. Results of CD14/CD16/CD45/CD300e/HLADR/GFAP staining on blood samples of 9 healthy controls and 9 glioma patients at diagnosis. The anti-GFAP antibody was directed against an N-terminal epitope on the protein. Panel A: examples of GFAP staining in a healthy control (left panel) and in a glioma patient (right panel). In the glioma patient, a cluster of GFAP positive early CTMs is identified, whereas such cells are not detected in the healthy control. Panel B: the percentage of GFAP+ cells within the early CTM population is plotted against the percentage of early CTMs per total CD300e+ cells (monocytes and CTMs) and against the size of the glioma. Virtually all glioma patients (7/9) had more than 1% GFAP+ early CTMs. Importantly, the frequency of GFAP positive cells also shows some correlation with the size of the glioma tumor mass.

FIG. 7. Examples of increase of CTSM in different types of diseases or medical conditions. A. Myocardial infarction. B. Bone fracture. C. Colon cancer. D. Metastasized breast cancer. E. Metastasized carcinoma in bone. F. Atherosclerosis. G. Alzheimer's disease. H. Multiple sclerosis. I. Autoimmune thyroiditis. J. Sjögren's syndrome. K. Type 1 diabetes mellitus. L. Systemic sclerosis. M. Glomerulonephrites in SLE patients. N. Lyme's disease. O. Tuberculosis. P. Pulmonary *Aspergillus*. Q. Muscle training. R. Surgical intervention with tissue damage.

EXAMPLE 1

Applications of CTSM-based Flow Cytometric Health Scanning: Determine the distribution of the CTSM subsets and thereby the physiological and non-physiological changes in the homeostasis of cell renewal, maintenance, repair, senescence and apoptosis.
1. Physiological Conditions: Growth, Aging, Pregnancy, Menopause, Physical Activity, Circadian Rhythms;
   Growth in children: organ development in infancy, childhood, adolescence, e.g. high activity in bone compartment (growth and remodeling) and consequent increase in the CTSM subset with bone-derived peptides;
   Highly active lymphoid precursor cell compartment for production of the high numbers of B- and T-lymphocytes in young children, which is reflected by the large thymus in these young children;
   Aging: senescence with organ involution and increased CTSM subsets;
   Pregnancy: placental function and dysfunction (early detection of placenta intoxication and delivery time);
   Thymus involution and reduced T-cell production: many T-cells (~90%) are negatively selected in the thymus;
   Ovarian function: detection of (premature) menopause by decreased ovarian CTSM.
   Bone formation and bone density: evaluation of bone formation and bone resorption during aging, e.g. in puberty/adolescence, aging, and early menopause.
2. Lifestyle Habits: For Example:
   Smoking: evaluation of lung damage through measurement of mucosal and epithelial cell balance;
   Alcohol: evaluation of liver damage in relation to alcohol intake;
   Sports: evaluation of muscle-derived CTSMs in enduring sports (e.g. marathon, triathlon) to design personalized training programs for top sportsmen with differential recovering capabilities;
   Sun/UV light exposure of the skin: measurement of skin epithelium peptides and melanin peptides to assess the UV exposure level and related damage (surface-extent and intensity of UV exposure).
3. Exposure to Environmental Agents
Direct evaluation of toxic components in tissue macrophages or indirect toxicity measurements in the involved tissues, such as in case of:
   Asbestos;
   Neurotoxic materials in paints;
   Consequences of irradiation after nuclear accidents.
4. General Tissue Damage (Skin, Mucosa, Muscles, and/or Bone):
   Trauma: extent of trauma and monitoring of progress of recovery;
   Surgical interventions: e.g. evaluation of post-surgery tissue damage as a measure of "quality-of-surgery", e.g. for evaluation of technical skills of residents in surgery.
   Effects of sepsis with multiple lesions throughout the body.
   Organ damage and other unwanted toxic side effects of medical intervention, such as in cancer treatment.
   Temperature influences on specific tissues, e.g. burn wounds (size, depth and body surface);
   Bone fractures and complexity and extend of the fractures (e.g. measurement of osteocalcin peptides and/or osteopontin peptides and/or bone alkaline phosphatase peptides).
5. Inflammatory and Auto-Immune Diseases:
   Extend of auto-immune diseases, such as systemic sclerosis;
   Sjögren disease: earlier diagnosis and sharper definition about involvement of lacrimal glands and salivary glands via measurement of specific epithelial peptides;
   Autoimmune cystitis; measurement of CTSM containing bladder epithelium peptides;

Glomerulonephritis: extent of kidney damage in autoimmune nephritis or early detection of kidney damage in patients with systemic lupus erythematosus (SLE) or early detection of rejection processes in patients after kidney transplantation;
Rheumatoid arthritis: detection of joint components (synovial membrane peptides) in CTSM;
Vasculitis: e.g. arteritis temporalis with CTSM's that contain endothelial cell peptides.
6. Neurological and Neurodegenerative Disorders:
Alzheimer disease: early diagnosis via CTSM with peptides from disease-associated proteins such as mutated Apoε4 and APP.
Multiple sclerosis: e.g. detection of myelin peptides in CTSM's.
Parkinson disease
Prion diseases, such as Jacob-Kreutzfeld disease
7. Infectious Diseases (Particularly With Persisting Smoldering and Insidious Character)
Combined detection of tissue-specific peptides and microorganism-specific peptides in the same TSM subsets:
*Mycobacterium* infections: difficult diagnosis in BCG positive patients and in children;
Q-fever: difficult diagnosis and difficult evaluation of treatment effectiveness;
Lyme's disease: detection of *Borrelia*-derived peptides in patients with vague complaints in whom the diagnosis of the disease remains a challenge;
Hepatitis B and Hepatitis C: monitoring of liver damage and/or viral proteins-derived peptides.
Diagnosis of invasive fungal and yeast infections: difficult diagnosis of *Aspergillus* infections; detection of fungal antigens in circulating tissue macrophages and identification of involved tissue via identification of involved CTSMs.
8. Metabolic Disorders:
Obesity: e.g. different disease-specific profiles of adipocyte-derived protein fragments;
Diabetes type 1 (juvenile insulin-dependent diabetes): detection in an early stage, before major damage of the insulin-producing cells in the pancreas has occurred;
Diabetes type 2 (late onset): increased CD14dim/CD16++ tissue macrophages with decreased function (cytokine production), if atherosclerotic complications are present;
Testosterone treatment in hypogonadism: increased tissue macrophages, but reduced function.
9. Diseases of Unknown Origin:
For example: detection of muscle-derived peptides and other disease markers (e.g. viral components):
Fibromyalgia;
Chronic fatigue syndrome: detection of viral components in tissue macrophages.
Fever of unknown origin (idiopathic): definition of the profile of CTSM, as a direct reflection of tissue-associated damage.
10. Malignancies:
In case of most carcinomas, epithelial membrane antigen can be used as general marker in combination with one or more tissue-specific markers
Carcinomas in general: e.g. peptides from EMA (epithelial membrane antigen);
Breast carcinoma: e.g. peptides from CA 15-3 antigen;
Thyroid carcinoma: e.g. peptides from RET as tumor marker;
Oesophagus carcinoma;
Gastric carcinoma;
Colon carcinoma: e.g. peptides from carcinoembryonic antigen (CEA);
Rectum/sigmoid carcinoma;
Lung carcinoma;
Cervix carcinoma or Uterus carcinoma:
Prostate carcinoma: e.g. PSA and ERG peptides;
Bladder carcinoma;
Melanoma: e.g. melanin peptides; MART-1/Melan-A
Pancreas carcinoma;
Kidney carcinoma, etc;
Neuroblastoma: e.g. peptides from disialoganglioside GD2;
Brain tumors e.g. GFAP (FIG. 6);
Mesothelioma: screening of asbestos-exposed workers and diagnosis in early stage via mesothelium-derived peptides in circulating tissue macrophages;
Rare cancers, which are difficult to diagnose, such as hypophysis tumors.
11. Early Detection and Monitoring of Tumor Metastases:
Combined detection of tumor-derived peptides and peptides from the infiltrated tissue in the same CTSM subset, e.g.:
Breast carcinoma metastasis in bone or liver: combined detection of breast-derived peptides and bone or liver-derived peptides in the same TSM subset;
Colon carcinoma metastasis in liver: combined detection of colon-derived peptides and liver-derived peptides in the same CTSM subset;
Prostate carcinoma metastasis in bone: combined detection of colon-derived peptides and bone-derived peptides in the same CTSM subset;
Intravascular B-cell lymphoma: combined detection of endothelium-derived peptides and B-cell-derived peptides in the same CTSM subset (high levels of tissue macrophages detected: >10% of blood leukocytes)
Intracerebral lymphoma: combined detection of CNS peptides and B-cell peptides in the same CTSM's.
12. Cardiovascular Diseases:
Angina pectoris: ECG aberrations with or without myocardial infarction;
Clotting disorder in patients at risk of thrombosis
Atherosclerotic lesions in patients with diabetes type II EXAMPLE 2: Glial Fibrillary Acidic Protein (GFAP) Staining in CTM of Patients With Glioma and Healthy Controls Materials and Methods Freshly collected blood samples from glioma patients (n=9) at diagnosis (before surgical intervention) and from healthy controls (n=9) were first subjected to surface membrane staining with the CD300e(UP-H2)-APC (Immunostep, Salamanca, Spain), CD14(MO-P9)-APCH7 (BD Biosciences San Jose, Calif., USA), CD16(3G8)-PECy7 (BD Biosciences San Jose, Calif., USA), CD45(HI30)-PacO (In-Vitrogen, Grand Island, N.Y., USA), and HLADR(L243)-PacB (BioLegend, San Diego, Calif., USA) according to the staining procedure described in Table 2 (Procedure A, steps 1 to 13). After the surface membrane staining the samples were subjected to an intracellular staining with the anti-GFAP(N-18)-PE antibody according to the staining procedure described in Table 2 (Procedure B, steps 16 to 43). The anti-GFAP antibody was directed against an N-terminal epitope of the protein and was obtained from Santa Cruz Biotechnology (Santa Cruz, Calif., USA). Cell fixation and permeabilization was performed with Fix & Perm (An der Grub, Vienna, AT). The stained cells were measured with a FACSCanto II multicolor flow cytometer (BD Biosciences)

and the data were analyzed with Infinicyt software (Cytognos, Salamanca, Spain). Gating of the monocytes and CTMs was based on gating on intermediate SSC and CD45 expression and subsequent gating on CD300e and HLADR positivity (see FIG. 4 for general staining pattern). Then further analysis for CD16 and CD14 expression was performed, followed by evaluation for the intracellular GFAP staining (see FIG. 6A).

Results

The percentage of early CTMs was expressed per total evaluated population (classical monocytes+all CTMs) and the GFAP positivity was expressed as percentage positive cells within the early CTM population. All healthy controls had less than 10% early CTMs and 6/9 healthy controls had less than 5% early CTMs. The percentages of GFAP positive early CTMs in the nine healthy controls was less than 1% (0.6%, 0.7% and 7 times 0%) (see FIG. 6B). The glioma patients had more than 5% early CTMs in 8/9 cases and more than 10% in 4/9 cases. The percentages of GFAP positive early CTMs varied from ~1% to ~31% (0.9%, 1.0%, 1.3%, 1.4%, 2.5%, 4.5%, 8.7%, 29.9%, 30.7%). The percentages of GFAP positive CTMs showed some correlation with the size of the glioma tumor mass (see FIG. 6B).

The invention claimed is:

1. A method for determining the health status of a subject, for early detection of tissue damage, for early diagnosis and monitoring of a disease, and/or for evaluation of treatment effectiveness in a subject using circulating tissue macrophages as a mirror of disrupted tissue homeostasis and disease, the method comprising the steps of:
   a) providing a peripheral blood sample from the subject which contains circulating tissue macrophages (CTM);
   b) staining said CTM with a panel of differentially-labeled distinct antibodies against the backbone markers CD14, CD16 and CD300e for the identification and enumeration of different CTM subsets;
   c) fixation, permeabilization and staining of the CTM using one or more detecting antibodies directed against one or more epitopes on at least one protease-induced protein fragments derived from intracellular degradation of a non-CTM protein by individual CTM in their tissues of origin, thereby identifying at least one subset of circulating tissue-specific macrophages (CTSM);
   d) multiparameter flow-cytometric analysis of said stained CTM and CTSM by gating for the backbone markers CD14, CD16 and CD300e to determine the amount of signals of each distinct labeled antibody associated with individual cells, wherein the analysis comprises performing a gating strategy based on the cell surface expression of CD300e, CD14 and CD16, in combination with side scatter (SSC) analysis, and wherein the gating strategy is composed of (i) an inclusion step to include both classical monocytes and CTMs based on CD300e expression in combination with side scatter (SSC) analysis, and (ii) a subsequent subset identification step to discriminate the classical CD14high/CD16−;
   e) determining the relative and absolute number of individual cells within each CTM subset and each specific subset of CTSM that express each of the measured intracellular epitopes;
   f) calculating (i) the relative and absolute number of cells within each CTM subset and each specific subset of CTSM which each originate from different normal and altered tissues as defined by a set of individual protease-induced protein fragments evaluated, and ii) the amount of antibody-related signal associated to every individual intracellular peptide evaluated to obtain a test CTSM staining profile, and;
   g) comparing the test CTSM staining profile with a normal CTSM staining profile for each tissue evaluated, wherein an aberrant test staining profile is indicative of tissue damage, an altered tissue homeostasis, the presence of a disease, and/or treatment effectiveness versus resistance.

2. The method according to claim 1, wherein the subset identification step comprises the identification of classical (CD14high/CD16−) monocytes and two main CTM subsets identified as CD14high/CD16low to CD14high/CD16high, CD14low/CD16high, and CD14−/CD16high to CD14−/CD16low cells.

3. The method according to claim 1, wherein step c) comprises intracellular staining of one or more of the following:
   a. one or more epitopes of a single protease-induced protein fragment derived from an intracellularly processed tissue-associated protein;
   b. one or more epitopes of two or more distinct protease-induced protein fragments derived from one intracellularly processed tissue-associated protein;
   c. one or more epitopes of two or more distinct protease-induced protein fragments derived from two or more intracellularly processed proteins derived from normal cells from a single organ or tissue;
   d. one or more epitopes of two or more distinct protease-induced protein fragments derived from two or more intracellularly processed proteins derived from abnormal cells from a single organ or tissue;
   e. one or more epitopes of two or more distinct protease-induced protein fragments derived from two or more intracellularly processed proteins derived from normal and abnormal cells from a single organ or tissue, including a combination of at least one antibody against peptide epitopes of a normal protein and at least one antibody against peptide epitopes from an aberrant protein, and;
   f. one or more epitopes of two or more distinct protease-induced protein fragments derived from two or more intracellularly processed proteins derived from normal or abnormal cells from two or more organs or tissues.

4. The method according to claim 3, wherein step c) comprises intracellular staining of one or more epitopes of a single protease-induced protein fragment derived from an intracellularly processed tissue-associated protein.

5. The method according to claim 1, wherein the at least one detecting antibodies allows for detection of one or more peptide epitopes derived from an aberrant protein.

6. The method according to claim 5, wherein the aberrant protein is selected from the group consisting of oncogenic proteins, mutated proteins, fusion proteins, proteins derived from an allergen and proteins derived from a pathogen.

7. The method according to claim 6, wherein the aberrant protein is selected from the group consisting of oncogenic proteins.

8. The method according to claim 6, wherein the pathogen is a virus, a bacterium, a parasite or a fungus.

* * * * *